(12) United States Patent
Vehige et al.

(10) Patent No.: US 10,213,405 B2
(45) Date of Patent: Feb. 26, 2019

(54) OPHTHALMIC COMPOSITIONS AND METHODS FOR TREATING EYES

(71) Applicant: Allergan, Inc., Irvine, CA (US)

(72) Inventors: Joseph G. Vehige, Laguna Niguel, CA (US); Peter A. Simmons, Yorba Linda, CA (US); Joan-En Chang-Lin, Tustin, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 15/585,888

(22) Filed: May 3, 2017

(65) Prior Publication Data

US 2018/0021282 A1 Jan. 25, 2018

Related U.S. Application Data

(60) Continuation of application No. 14/987,333, filed on Jan. 4, 2016, now Pat. No. 9,668,997, which is a continuation of application No. 14/248,227, filed on Apr. 8, 2014, now Pat. No. 9,254,324, which is a continuation of application No. 14/024,332, filed on Sep. 11, 2013, now Pat. No. 8,729,125, which is a continuation of application No. 13/842,555, filed on Mar. 15, 2013, now Pat. No. 8,569,370, which is a division of application No. 10/990,811, filed on Nov. 16, 2004, now Pat. No. 8,569,367.

(51) Int. Cl.
| | |
|---|---|
| *A61K 31/205* | (2006.01) |
| *A61K 9/00* | (2006.01) |
| *A61K 9/08* | (2006.01) |
| *A61K 47/26* | (2006.01) |
| *A61K 47/38* | (2006.01) |
| *A61K 31/047* | (2006.01) |
| *A61K 31/14* | (2006.01) |
| *A61K 31/717* | (2006.01) |
| *A61K 31/728* | (2006.01) |
| *A61K 38/17* | (2006.01) |
| *A61K 31/70* | (2006.01) |
| *A61K 47/02* | (2006.01) |

(52) U.S. Cl.
CPC .......... *A61K 31/205* (2013.01); *A61K 9/0048* (2013.01); *A61K 9/08* (2013.01); *A61K 31/047* (2013.01); *A61K 31/14* (2013.01); *A61K 31/70* (2013.01); *A61K 31/717* (2013.01); *A61K 31/728* (2013.01); *A61K 38/1732* (2013.01); *A61K 47/02* (2013.01); *A61K 47/26* (2013.01); *A61K 47/38* (2013.01)

(58) Field of Classification Search
CPC ...... A61K 31/205; A61K 9/0048; A61K 9/08; A61K 47/26; A61K 47/38; A61K 31/047; A61K 31/14; A61K 31/717; A61K 31/728; A61K 38/1732; A61K 31/07; A61K 47/02
See application file for complete search history.

(56) References Cited

U.S. PATENT DOCUMENTS

| | | | |
|---|---|---|---|
| 3,278,447 A | 10/1966 | McNicholas | |
| 4,201,706 A | 5/1980 | Trager et al. | |
| 5,037,851 A | 8/1991 | Cavazza | |
| 5,145,871 A | 9/1992 | Cavazza | |
| 5,192,535 A * | 3/1993 | Davis | A61K 9/0048 424/427 |
| 5,432,199 A | 7/1995 | Cavazza | |
| 5,527,512 A | 6/1996 | Bachtel et al. | |
| 5,527,831 A | 6/1996 | Franz et al. | |
| 5,827,512 A | 10/1998 | Gleich | |
| 6,156,293 A | 12/2000 | Jutila et al. | |
| 6,193,957 B1 | 2/2001 | Ahmed | |
| 6,228,392 B1* | 5/2001 | Morcos | A61K 47/10 424/450 |
| 6,274,725 B1 | 8/2001 | Sanghvi et al. | |
| 6,365,622 B1* | 4/2002 | Cavazza | A61K 31/385 514/440 |
| 6,555,526 B2 | 4/2003 | Matsuo et al. | |
| 6,585,987 B1* | 7/2003 | Fransoni | A61K 31/728 424/401 |
| 7,045,121 B2 | 5/2006 | Chang et al. | |
| 8,569,367 B2 | 10/2013 | Vehige et al. | |
| 8,569,370 B2 | 10/2013 | Vehige et al. | |
| 8,729,125 B2* | 5/2014 | Vehige | A61K 9/0048 514/556 |
| 9,254,324 B2* | 2/2016 | Vehige | A61K 9/0048 |
| 2002/0002185 A1 | 1/2002 | Reed et al. | |
| 2002/0071874 A1* | 6/2002 | Olejnik | A61K 9/0048 424/661 |
| 2003/0069410 A1 | 4/2003 | Ravikumar | |
| 2003/0190258 A1 | 10/2003 | Smith | |
| 2003/0195160 A1 | 10/2003 | Johnson et al. | |
| 2004/0005289 A1 | 1/2004 | Chang et al. | |
| 2004/0137079 A1 | 7/2004 | Cook et al. | |
| 2004/0192647 A1 | 9/2004 | Babizhayev | |
| 2005/0009836 A1 | 1/2005 | Laskar et al. | |
| 2006/0035842 A1 | 2/2006 | Tsuzuki et al. | |

FOREIGN PATENT DOCUMENTS

| | | |
|---|---|---|
| EP | 0028110 | 5/1981 |
| EP | 0436726 | 7/1991 |
| EP | 0585896 | 3/1994 |
| EP | 0778021 | 6/1997 |
| EP | 0848952 | 6/1998 |

(Continued)

OTHER PUBLICATIONS

JP10036255 Machine translation (Year: 1998).*

(Continued)

*Primary Examiner* — Sean M Basquill
(74) *Attorney, Agent, or Firm* — Lorenz Siddiqi

(57) ABSTRACT

Ophthalmic compositions including compatible solute components and/or polyanionic components are useful in treating eyes, for example, to relieve dry eye syndrome, to protect the eyes against hypertonic insult and/or the adverse effects of cationic species on the ocular surfaces of eyes and/or to facilitate recovery from eye surgery.

7 Claims, 8 Drawing Sheets
Specification includes a Sequence Listing.

(56) References Cited

FOREIGN PATENT DOCUMENTS

| | | | |
|---|---|---|---|
| JP | 10036255 | * | 2/1998 |
| JP | 2763400 | | 3/1998 |
| JP | 2010-036255 | | 2/2010 |
| RU | 2234337 | | 8/2004 |
| WO | 1998-041208 | | 9/1998 |
| WO | 0029030 | | 5/2000 |
| WO | 0157172 | | 8/2001 |
| WO | 2002-038161 | | 5/2002 |
| WO | 03004512 | | 1/2003 |
| WO | 03028633 | | 4/2003 |
| WO | 2003-051332 | | 6/2003 |
| WO | 2004006801 | | 1/2004 |
| WO | 2004030666 | | 4/2004 |
| WO | 2004-084877 | | 7/2004 |
| WO | 2008106228 | | 9/2008 |
| WO | 2010-141648 | | 12/2010 |

OTHER PUBLICATIONS

Samir Melki, et al, LASIK Complications: Etiology, Management, and Prevention, 46 Surv. Ophthalmol. 95 (Year: 2001).*
Eric Donnenfeld, et al, The Effect of Hinge Position on Corneal Sensation and Dry Eye After LASIK, 110 Ophthalmol. 1023 (Year: 2003).*
Carolyn Begley, et al, Responses of Contact Lens Wearers to a Dry Eye Survey, 77 Optom. Vis. Sci. 40 (Year: 2000).*
Albietz, Julie et al, A Comparison of the Effect of Refresh plus and Bion Tears on Dry Eye Symptoms and Ocular Surface Health in Myopic LASIK Patients, the CLAO Journal, 2002, 96-100, 28(2).
Alfieri, Roberta et al, Compatible Osmolytes Modulate the Response of Porcine Endothelial Cells to Hypertonicity and Protect Them From Apoptosis, J. Physiol., 2002, 499-508, 540.
Barker, Robert et al, Acidic Polyamino Acids Inhibit Human Eosinophil Granule Major Basic Protein Toxicity. Evidence of a Functional Role for ProMBP, J. Clin. Invest, Sep. 1991, 798-805, 88.
Bielory, L., Allergic and Immunologic Disorders of the Eye. Part II: Ocular Allergy, J. Allergy CLin. Immunol. 2000, 106: 1019-1035.
Biocompare®: Product Review: Upstate's Beadlyte Human/Mouse Cytokine Detection Kits, Jun. 15, 2004, 3 Pages, Biocompare, Inc.
Brown, Theodore et al, Glossary: Salt, Chemistry: The Central Science, 2006, G-10, 10th Edition.
Burg, Maurice, Molecular Basis of Osmotic Regulation, American Physiological Society, 1995, F983-F996, 268.
Cammarata, Patrick et al, Osmoregulatory Alterations in taurine Uptake by Cultured Human and Bovine lens Epithelial Cells, Invest. Ophthalmol. Vis. Sci., 2002, 425-433, 43.
Gilbard, Jeffrey, Tear Film Osmolarity and Keratoconjunctivitis Sicca, the CLAO Journal, Jul. 1985, 243-250, 11 (3).
International Search Report and Written Opinion dated Jul. 6, 2006 for PCT/US05/41064 filed on Nov. 14, 2015 in the name of Allergan, Inc.
Matsuo, Toshihiko et al, Trehalose Eye Drops in the Treatment of Dry Eye Syndrome, Ophthalmology, 2002, 2024-2029, 109.
McGrogan, Michael et al, Isolation of a Complementary DNA Clone Encoding a Precursor to Human Eosinophil Major Basic Protein, J. Exp. Med., Dec. 1988, 2295-2308, 168.
Nakajima, Toshiharu et al, Gene Expression Screening of Human Mast Cells and Eosinophils Using High-Density Oligonucleotide Probe Arrays: Abundant Expression of Major Basic Protein in Mast Cells, Blood, Aug. 2001, 1127-1134, 98 (4).
Peluso, Gianfranco et al, Carnitine: An Osmolyte That Plays a Metabolic Role, Journal of Cellular Biochemistry, 2000, 1-10, 80.
Pessotto, P. et al, The Presence of L-Carnitine in Ocular Tissues of the Rabbit, Journal of Ocular Pharmacology, 1994, 643-651, 10 (4).
Popken-Harris, Pamela et al, Biochemical Properties, Activities, and Presence in Biologic Fluids of Eosinophil Granule Major Basic Protein, J. Allergy Clin. Immunol., 1994, 1282-1289, 94 (6).
Popken-Harris, Pamela et al, Regulation and Processing of a Precursor Form of Eosinophil Granule Major Basic Protein (ProMBP) in Differentiating Eosinophils, Blood, Jul. 1998, 623-631, 92 (2).
Rhyne, P.W. et al, Analysis of Apoptotic Cells Using Beadlyte Suspension Arrays, Biotechnigues, Sep. 2003, 624-629 (Abstract), 35 (3).
Shioda, Ryo et al, Osmosensitive Taurine Transporter Expression and Activity in Human Corneal Epithelial Cells, Investigative Ophthalmology & Visual Science, Sep. 2002, 2916-2922, 43 (9).
Voet et al, Transport Across the Mitochondrial Membrane, Biochemistry, 1990, 622.

* cited by examiner

SEQUENCE LISTING

```
<160> NUMBER OF SEQ ID NOS: 1

<210> SEQ ID NO 1
<211> LENGTH: 89
<212> TYPE: PRT
<213> ORGANISM: Homo sapiens
<300> PUBLICATION INFORMATION:
<301> AUTHORS: Popken-Harris, P., et al.
<302> TITLE: Regulation and processing of a precursor form of eosinophil
      granule major basic protein (ProMBP) in differentiating
      eosinophils
<303> JOURNAL: Blood
<304> VOLUME: 92
<305> ISSUE: 2
<306> PAGES: 623-631
<307> DATE: 1998-07-15
```

```
<400> SEQUENCE: 1

Leu His Leu Arg Ser Glu Thr Ser Thr Phe Glu Thr Pro Leu Gly Ala
1               5                   10                  15

Lys Thr Leu Pro Glu Asp Glu Glu Thr Pro Glu Gln Glu Met Glu Glu
                20                  25                  30

Thr Pro Cys Arg Glu Leu Glu Glu Glu Glu Trp Gly Ser Gly Ser
        35                  40                  45

Glu Asp Ala Ser Lys Lys Asp Gly Ala Val Glu Ser Ile Ser Val Pro
    50                  55                  60

Asp Met Val Asp Lys Asn Leu Thr Cys Pro Glu Glu Glu Asp Thr Val
65                  70                  75                  80

Lys Val Val Gly Ile Pro Gly Cys Gln
                85
```

OPHTHALMIC COMPOSITIONS AND METHODS FOR TREATING EYES

CROSS REFERENCE TO RELATED APPLICATION

This application is a continuation of U.S. patent application Ser. No. 14/987,333, filed Jan. 4, 2016, which is a continuation of U.S. patent application Ser. No. 14/248,227, filed Apr. 8, 2014, now U.S. Pat. No. 9,254,324, issued Feb. 9, 2016, which is a continuation of U.S. patent application Ser. No. 14/024,332, filed Sep. 11, 2013, now U.S. Pat. No. 8,729,125, issued May 20, 2014, which is a continuation of U.S. patent application Ser. No. 13/842,555, filed Mar. 15, 2013, now U.S. Pat. No. 8,569,370, issued Oct. 29, 2013, which is a divisional of U.S. patent application Ser. No. 10/990,811, filed on Nov. 16, 2004, now U.S. Pat. No. 8,569,367, issued Oct. 29, 2013, the disclosures of which are hereby incorporated in their entirety by reference.

BACKGROUND OF THE INVENTION

The present invention relates to ophthalmic compositions and methods useful for treating eyes. More particularly, the present invention relates to ophthalmic compositions including mixtures of components which are effective in providing desired protection to ocular surfaces of human or animal eyes, and to methods for treating human or animal eyes using ophthalmic compositions, for example, the present ophthalmic compositions.

Mammalian eyes, such as human and other mammalian (animal) eyes, advantageously are adequately lubricated to provide eye comfort and to more effectively provide good, clear vision. Ordinarily, such lubrication is obtained naturally from a tear film, which is formed over the outer, exposed ocular surface of the eye. This tear film is a complex fluid that is normally continuously replenished by the lacrimal, meibomian, and other glands, and when intact provides essential hydration and nutrients to the ocular surface. In addition to coating and protecting the delicate ocular surface, the tear film/air interface also serves as the initial refractive surface of the eye. However, in many instances, this tear film is not present in a sufficient amount, and a condition known as "dry eye" can result.

A relatively large number of compositions have been suggested for use in the treatment and management of dry eye syndrome. For example, artificial tears, that is materials having chemical compositions which mimic or resemble the functioning of natural tears, have been used. Such artificial tears often require very frequent use since they are rapidly lost from the eye. In addition, although they wet the eye, their value in lubricating the eye is somewhat less than desired. Compositions which include specific lubricants have been suggested. For example, a number of compositions including carboxy methylcelluloses (CMCs) have been used in eyes.

Under normal conditions, the ocular surface of a human or animal eye is bathed in tears of a normal osmotic strength, for example, substantially isotonic. If this osmotic strength is increased, cells on the ocular surface are exposed to a hyperosmotic or hypertonic environment resulting in adverse reduction in cell volume due to trans-epithelial water loss, and other undesired changes. The compensatory mechanisms are limited, in many respects, leading to ocular surface compromise and discomfort. For example, the cells may attempt to balance osmotic pressure by increasing internal electrolyte concentration. However, at elevated electrolyte levels, cell metabolism is altered in many ways, including the reduction in enzyme activity and membrane damage. In addition, a hypertonic environment has been shown to be pro-inflammatory to the ocular surface.

The cells of many life forms can compensate for hypertonic conditions through the natural accumulation or manufacture of so-called "compatible solutes", that work like electrolytes to balance osmotic pressure yet do not interfere with cellular metabolism like electrolytes. Compatible solutes or compatible solute agents, generally, are uncharged, can be held within a living cell, for example, an ocular cell, are of relatively small molecular weight and are otherwise compatible with cell metabolism. Compatible solutes are also considered to be osmoprotectants since they may allow cell metabolism and/or enhance cell survival under hypertonic conditions that would otherwise be restricting.

For example, a class of organisms called halophiles exist that inhabit hypersaline environments such as salt lakes, deep sea basins, and artificially-created evaporation ponds. These organisms may be eukaryotic or prokaryotic, and have mechanisms for synthesizing and/or accumulating a variety of compatible solute agents, including polyols, sugars, and amino acids and their derivatives such as glycine, betaine, proline, ectoine, and the like.

Glycerin (glycerol) is a widely used osmotic agent that has been identified as a compatible solute in a variety of cells from a number of different species. It is also regarded as a humectant and ophthalmic lubricant. In the U.S., it is applied topically to the ocular surface to relieve irritation at concentrations up to 1%, and has been used at higher concentrations to impart osmotic strength in prescription medications. Given its small size and biological origin, it should easily cross cell membranes, and transport channels have been recently identified in some cell types to facilitate glycerol movement.

Although glycerol may serve as the sole compatible solute, it may be excessively mobile, that is, cross membranes too freely, to provide an extended benefit in certain systems. An example is the human tear film where natural levels of glycerol are low. When a topical preparation is applied, migration into the cell is likely to occur fairly rapidly. However, as concentration in the tear falls, glycerol may be lost over time from cell to tear film, limiting the duration of benefit.

Another major class of compounds with osmoprotective properties in a variety of tissues is certain amino acids. In particular, betaine (trimethyl glycine) has been shown to be actively taken up by renal cells in response to osmotic challenge, and taurine is accumulated by ocular cells under hypertonic conditions.

There continues to be a need to provide ophthalmic compositions, for example, artificial tears, eye drops and the like, which are compatible with ocular surfaces of human or animal eyes and advantageously are effective to allow such ocular surfaces to better tolerate hypertonic conditions.

Hypotonic compositions have been used on eyes as a method to counteract the effects of hypertonic conditions. These compositions effectively flood the ocular surface with water, which rapidly enters cells when supplied as a hypotonic artificial tear. Due to the rapid mobility of water into and out of cells, however, any benefit of a hypotonic composition will be extremely short-lived. Further, it has been demonstrated that moving cells from a hypertonic environment to an isotonic or hypotonic environment downregulates transport mechanisms for cells to accumulate compatible solutes. Thus, use of a hypotonic artificial tear reduces the ability of cells to withstand hypertonicity when it returns shortly after drop instillation.

The clinical observation that agents such as carboxy methylcellulose sodium (CMC) and sodium hyaluronate (SH) are useful in treating signs and symptoms of dry eye syndrome or disease is well established. These two polyanionic agents have also been shown to be particularly useful in conditions where induced corneal compromise (CMC and LASIK surgical procedures) or allergic corneal insult (SH and shield ulcers in allergy) exist.

In addition, the tear film of the presumed normal human or animal eye may have elevated (detectable) levels of Major Basic Protein (MBP) whereas it was previously believed that this protein was only expressed under conditions of allergy with eosinophilic involvement (late phase allergy). MBP is now recognized to be produced by Mast Cells (MC) as well as eosinophils, which are known to commonly reside within ocular surface tissues and are recognized to de-granulate, releasing MBP and other cationic compounds, under antigenic stimulation, mechanical trauma, and other conditions.

Another group of cationic proteins active on the ocular surface are one or more of the defensins, which are normally part of the body's antimicrobial defense system. Defensins are found at increased levels in the tear film of dry eye patients, and may either directly or through interaction with other substances have adverse effects on the health of the ocular surface.

There are recognized treatments designed to reduce the likelihood of MC de-granulation, most of which are used on the ocular surface in conjunction with treating seasonal or perennial allergic conjunctivitis. However, once de-granulation occurs, there are no recognized treatments to sorb, clear or deactivate released cationic mediators including MBP. Saline irrigation would dilute the agents but is impractical in most cases. Also, recent data indicates that there is detectable MBP on the ocular surface even in non-allergic eyes, meaning that an overabundance of MBP and potential low-grade ocular surface damage may occur to individuals at any given time.

It would be advantageous to provide ophthalmic compositions which are effective to mitigate against or reduce the adverse effects of cationic, for example, polycationic, materials on ocular surfaces of human or animal eyes.

SUMMARY OF THE INVENTION

New ophthalmic compositions for treating eyes, and methods of treating eyes have been discovered. The present compositions very effectively treat eyes, for example, eyes afflicted or susceptible to diseases/conditions, such as, without limitation, dry eye syndrome, low humidity environments, and stress/trauma, for example, due to surgical procedures, and the like. In particular, these compositions would be useful for mitigating the damaging effects of a hypertonic tear film, regardless of cause. The present compositions are relatively straightforward, can be easily and cost effectively manufactured, and can be administered, for example, topically administered, to an ocular surface of an eye very conveniently.

In one broad aspect of the present invention, ophthalmic compositions are provided comprising a carrier component, advantageously an aqueous carrier component, and an effective amount of a tonicity component including a material selected from compatible solute components, for example, one or more of certain compatible solute agents, and mixtures thereof. In one very useful embodiment, the tonicity component comprises a material selected from erythritol components and mixtures thereof. In one additional embodiment, the tonicity component comprises a material selected from combinations of at least two different compatible solute agents.

In another broad aspect of the invention, ophthalmic compositions are provided comprising a carrier, for example, an aqueous carrier, component, and an effective amount of a material selected from inositol components, xylitol components and mixtures thereof. The osmolality of such compositions are often higher or greater than isotonic, for example, in a range of at least 310 to about 600 or about 1000 mOsmols/kg.

In a further broad aspect of the invention, ophthalmic compositions are provided which comprise a carrier, for example, an aqueous carrier, component, and an effective amount of a tonicity component comprising a material selected from carnitine components and mixtures thereof. In a particularly useful embodiment, the composition has a non-isotonic osmolality.

In an additional aspect of the present invention, ophthalmic compositions are provided which comprise a carrier, for example, an aqueous carrier, component, and an effective amount of a tonicity component comprising a material selected from a mixture or combination of compatible solute agents, for example, selected from mixtures of one or more polyol components and/or one or more amino acid components.

In each of the above-noted aspects of the invention, the present compositions advantageously have chemical make-ups so as the material or the mixture of organic compatible solute included in the tonicity component is effective, when the composition is administered to an eye, to allow an ocular surface of the eye to better tolerate a hypertonic condition on the ocular surface relative to an identical composition without the material or the mixture of organic compatible solute agents.

A still further broad aspect of the invention provides ophthalmic compositions comprising carrier component, a tonicity component and a polyanionic component. The tonicity component is present in an amount effective to provide the composition with a desired osmolality, and comprises a compatible solute component. The polyanionic component is present in an amount, when the composition is administered to a human or animal eye, to reduce at least one adverse effect of a cationic, for example, a polycationic, material on an ocular surface of a human or animal eye relative to an identical composition without the polyanionic component. This cationic material could be from any source, for example, may be endogenous, an environmental contaminant, or as an undesired consequence of applying an agent to the eye, for example a preserved solution or contact lens care product. In one very useful embodiment, hyaluronic acid is not the sole polyanionic component. Other polyanionic components are more suited for use in the present compositions, for example, are more suited than hyaluronic acid or its salts for topical administration to an ocular surface of a human or animal eye. In another embodiment of the present invention, the composition has an osmolality in a range of about 300 to about 600 or about 1000 mOsmols/kg.

One further broad aspect of the invention provides ophthalmic compositions comprising a carrier component, and a polyanionic component selected from polyanionic peptides, polyanionic peptide analogs, portions of polyanionic peptide analogs, carboxymethyl-substituted polymers of sugars, including but not limited to, glucose and the like sugars and mixtures thereof. Such polyanionic components are present in an amount effective, when the compositions are administered to a human or animal eye, to reduce at least one adverse effect of a cationic, for example, polycationic, species and/or substance on an ocular surface of the eye relative to an identical composition without the polyanionic component.

Methods of treating human or animal eyes are also provided. Such methods comprise administering a composition, for example, a composition in accordance with the present invention, to a human or animal eye to provide at least one benefit to the eye.

Any and all features described herein and combinations of such features are included within the scope of the present invention provided that the features of any such combination are not mutually inconsistent.

These and other aspects of the present invention, are apparent in the following detailed description, accompanying drawings, examples and claims.

DETAILED DESCRIPTION OF THE INVENTION

Figure 1:
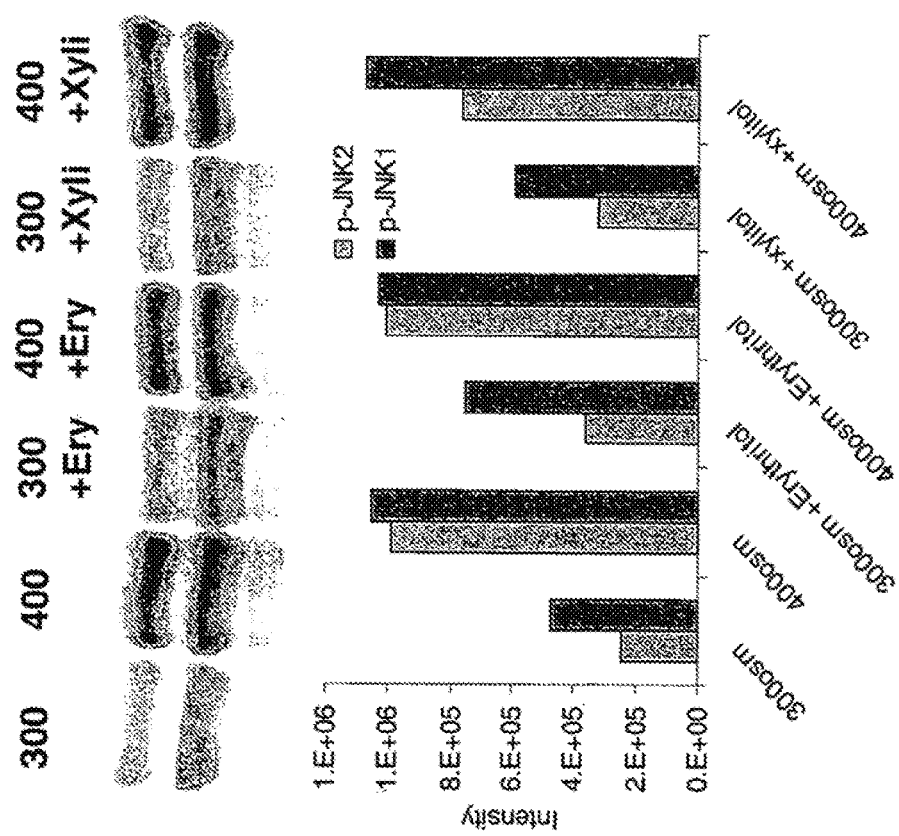
FIG. 1 is a graphical presentation of the intensity with regard to phosphorylated c-jun N-terminal kinases (p-JNK1 and p-JNK2) of certain ophthalmic compositions.

The present invention is directed to ophthalmic compositions useful in treating human or animal eyes. As noted above, in one aspect of the invention, compositions are provided which include a carrier component, for example, an aqueous-based or aqueous carrier component, and a tonicity component comprising a material selected from at least one compatible solute component, for example organic compatible solute component. Such compositions advantageously include an effective amount of the material so that, when the composition is administered to an eye, the material is effective to allow an ocular surface of an eye to better tolerate a hypertonic condition on the ocular surface relative to an identical composition without the material.

Although such compositions may have any suitable tonicity or osmolality, for example, a hypotonic osmolality, a substantially isotonic osmolality or a hypertonic osmolality, very useful compositions have osmolalities other than isotonic osmolality, for example, greater than isotonic osmolality. In one embodiment, the present compositions have osmolalities in a range of at least about 300 or about 310 to about 600 or about 1000 mOsmols/kg.

Polyols, such as erythritol components, xylitol components, inositol components, and the like and mixtures thereof, are effective tonicity/osmotic agents, and may be included, alone or in combination with glycerol and/or other compatible solute agents, in the present compositions. Without wishing to limit the invention to any particular theory of operation, it is believed that because of their increased size, relative to glycerol, these polyol components when used topically on the eye, accumulate in the cells more slowly than glycerol, but remain within the cells for prolonged periods of time relative to glycerol.

In one very useful embodiment, mixtures of two or more different compatible solute components, for example, glycerol and/or one or more other polyol components and/or one or more other compatible solute components, for example, one or more uncharged or zwitterionic amino acid components and the like, may be advantageously used together to provide one or more benefits to the eye that are not obtained using compositions including only a single compatible solute component.

As used herein, the term "component" as used herein with reference to a given compound refers to the compound itself, isomers and stereoisomers, if any, of the compound, suitable salts of the compound, derivatives of the compound and the like and mixtures thereof.

As use herein, the term "derivative" as it relates to a given compound refers to a compound having a chemical make-up or structure sufficiently similar to the given compound so as to function in a manner substantially similar to a substantially identical to the given compound in the present compositions and/or methods.

Comfort and tolerability can be considered in formulating the present compositions. The amount of organic compatible solute component employed in the present compositions should be effective in providing at least one benefit to the eye of a patient without unduly adversely affecting the patient, for example, without unduly inducing discomfort, reflex tearing and the like adverse affects.

For a formulator schooled in the art, it is possible to make thick fluids and gels that are retained for greater periods on the ocular surface than thin fluids, with the trade-off often being a transient vision blur. Thick fluids and gels however have the advantage of less frequent dosing to deliver a given amount of substance.

Xylitol or erythritol used alone may require prolonged contact time to allow them to function effectively as a compatible solute component, for example, due to the time needed for cellular uptake. However once in situ, for example, within ocular surface cells, the beneficial action of balancing hypertonic conditions advantageously is longer than with an equivalent amount of glycerol, which moves more quickly into and out of cells. Such longer lasting benefit, and less frequent dosing, can be obtained without blurred vision.

In one embodiment, the present compositions include a combination or mixture of compatible solute agents, with each agent advantageously being of different chemical type and/or having a different molecular size and/or mobility. Small mobile agents offer rapid but short duration effectiveness, e.g., protection from hypertonic insult, whereas large less mobile agents offer delayed but longer lasting protection effectiveness.

Xylitol, erythritol and glycerol all have high hydroxyl group concentrations: one per carbon. Hydroxyl groups allow for greater water binding and increase compound solubility. In compositions for treatment of dry eye syndrome, such high hydroxy group concentration may enhance performance of the composition by preventing water loss from the tissues.

Among the polyols, the 5-carbon xylitol, 4-carbon erythritol, and 3-carbon glycerol are preferred for ophthalmic use. The 2-carbon form (ethylene glycol) is a well-known toxin and is not suitable. The 6-carbon forms (mannitol, sorbitol, and related deoxy compounds) may be useful in combination with the smaller molecules. In one embodiment, combinations of polyols with 3 to 6 carbons, and 1 and 2 carbon deoxy derivatives including, without limitation, isomers, stereo-isomers and the like, as appropriate, may be useful in the present invention.

Uncharged or zwitterionic amino acids are useful as organic compatible solute components in accordance with the present invention.

Carnitine components, for example, carnitine itself, isomers/stereo-isomers thereof, salts thereof, derivatives thereof and the like and mixtures thereof, are very useful compatible solute components for use in the present ophthalmic compositions. Carnitine is well-established as necessary for various parts of fatty acid metabolism, so it has a significant role in the metabolism of liver and muscle cells. Carnitine may serve as an energy source for many types of cells, including ocular cells. Carnitine components may have unique properties in multiple roles, for example as osmoprotectants, in fatty acid metabolism, as an antioxidant, in promoting wound healing, as a protein chaperone, and in neuroprotection.

The organic compatible solute component may be advantageously provided in the present compositions by using a combination of such agents or materials of differing size, mobility, and mechanism of action. Small mobile agents, such as smaller polyols, would be predicted to offer rapid but short duration osmoprotection. Several of the amino acids and related compounds may function as long-acting intracellular compatible solutes and protein stabilizers. In the present invention, carnitine components may be used alone or in combination with one or more other amino organic compatible solute components and/or polyols, for example, as described herein.

Amine-based organic compatible solute components and/or components that may be used include, but are not limited to, betaine, taurine, carnitine, sarcosine, proline, trimethylamines in general, other zwitterionic amino acids and the like and mixtures thereof. Polyols that may be useful in combination with carnitine and/or one of the other amine-based organic compatible solute components include, but are not limited to, glycerol, propylene glycol, erythritol, xylitol, myo-inositol, mannitol, sorbitol and the like and mixtures thereof.

The amount of the compatible solute component included in the present compositions may be any suitable amount. However, such amount advantageously is effective to provide a benefit to the eye as a result of the administration of the composition containing the compatible solute component to the eye. Excessive amounts of compatible solute components are to be avoided, since such amounts can cause discomfort to the patient and/or potential harm to the eye being treated. The compatible solute component advantageously is present in an amount effective in providing the desired osmolality to the composition.

The specific amount of compatible solute component employed may vary over a wide range depending, for example, on the overall chemical make-up and intended use of the composition, on the desired osmolality of the composition, on the specific compatible solute or combination of such solutes being employed and the like factors. In one embodiment, the total amount of compatible solute component included in the present compositions may be in a range of about 0.01% (w/v) or about 0.05% (w/v) to about 1% (w/v) or about 2% (w/v) or about 3% (w/v) or more.

Corneal surface cells respond to osmotic forces by regulating salt and water transport in an effort to maintain a constant cell volume. In conditions of chronic hypertonicity, for example, such as exist in dry eye disease, transport mechanisms for uptake of compatible solutes, including various amino acids and polyols, are up-regulated. In one embodiment of the present invention, ophthalmic compositions, for example, artificial tears, containing a compatible solute component are formulated to have a tonicity higher or in excess of isotonicity, advantageously in a tonicity range of about 300 or about 310 to about 600 or about 1000 mOsmols/kg. Without wishing to limit the invention to any particular theory of operation, it is believed that, under such conditions, both immediate and long-term mechanisms to accumulate compatible solutes in cells are stimulated, allowing enhanced uptake and retention compared to cellular activity under isotonic or hypotonic conditions. Once the compatible solute component is accumulated by the cells, the cells have enhanced protection from ongoing hypertonic insult, for example, caused by dry eye syndrome and/or one or more other conditions/diseases. Results of this enhanced protection include improved cellular metabolism and survival for a period of hours to days following application of an ophthalmic composition of the present invention.

In the normal lacrimal system, tear production, tear drainage, and tear evaporation is balanced in order to provide a moist, lubricated ocular surface. Typical values for tear osmolarity range from 290 to 310 mOsmols/kg in normal individuals, and these may change throughout the day or in response to changing environmental conditions. In the normal individual, neural feedback from the ocular surface to the lacrimal glands controls tear production in order to maintain a stable ocular surface fluid. It has been proposed that tear film tonicity is one of the principal stimuli for this regulatory feedback. In dry eye disease, dysfunction of the production apparatus (the various glands), the drainage system, the neural signaling mechanism, or the ocular surface itself leads to an inadequate tear film, ocular surface compromise, and subjective discomfort.

On the cellular level, dry eye disease is usually characterized by a chronically hypertonic extracellular (tear film) environment. Published reports of the tonicity of the tear film of dry eye patients gives a range of 300 to 500 mOsmols/kg, with most values between 320 and 400 mOsmols/kg. Under these conditions, cells will tend to lose water and/or gain salts, and may undergo cell volume changes. Hypertonicity has been shown to alter cellular metabolic processes, reduce the functioning of enzymatic processes, and lead to apoptosis and cell death.

As a defense against hypertonic challenge, corneal cells have been demonstrated to up-regulate transport mechanisms for non-ionic solutes such as amino acids and polyols, and accumulate these solutes intracellularly in order to maintain cell volume without changing electrolyte balance. Under these conditions, cellular metabolism is less affected than with volume and electrolyte changes, and such compounds are referred to as compatible solutes. Compatible solutes include but are not limited to the amino acids betaine (trimethylglycine), taurine, glycine, and proline, and the polyols glycerol, erythritol, xylitol, sorbitol, and mannitol. Compatible solutes are also considered to be osmoprotectants since they may allow cell metabolism or enhance cell survival under hypertonic conditions that would otherwise be restricting.

Cells accumulate certain compatible solutes by biosynthesis within the cell and others by increased trans-membrane transport from the extracellular fluid (in this case the tear fluid). In both cases, specific synthetic or transport proteins are involved in this process. Experimental evidence indicates that these proteins are activated in the presence of hypertonic conditions, and that transcription and translation events to produce these proteins are up-regulated by hypertonic conditions. Conversely, experimental evidence indicates that corneal and other cells will expel compatible solutes when exposed to hypotonic conditions, or when moving from a hypertonic to an isotonic environment.

In dry eye disease, corneal surface cells are exposed to a hypertonic environment, and are stimulated to accumulate osmoprotectant substances as they are available. The addition of an iso- or hypo-tonic artificial tear to the ocular surface provides relief from symptoms due to enhanced lubrication, but tends to down-regulate mechanisms in these cells for accumulation of osmoprotectants. This may result in further vulnerability to osmotic insult in the minutes to hours following drop use as the tear film returns to its hypertonic dry eye state.

Current FDA guidance stipulates that "an ophthalmic solution should have an osmotic equivalence between 0.8 and 1.0 percent sodium chloride to comply with labeling claims of 'isotonic solution'." This is equivalent to a range from 274 to 342 mOsm/kg. Further, FDA guidelines state that "two to 5 percent sodium chloride ophthalmic preparations are hypertonic and are acceptable OTC products when labeled as 'hypertonic solutions'." This range equates to 684 to 1711 mOsm/kg. For the purposes of the present invention, a "supra-tonic" solution is defined to have an osmolality intermediate between these two ranges, or approximately 300 or 310 to about 600 or about 800 or about 1000 mOsmols/kg, equivalent to about 0.9 to about 1.8 percent sodium chloride (1.8% is the maximum FDA guidance for topical ophthalmic solutions not labeled as hypertonic).

The present invention takes these concepts into account by formulating an artificial tear at supra-tonic levels more compatible with the existing hypertonic state of the dry eye ocular surface. In addition to being formulated in the supra-tonic range (about 300 or about 310 to about 600 or about 1000 mOsmols/kg total tonicity), the present compositions contain one or more organic compatible solute agents as described herein. The combination of supra-tonicity and inclusion of one or more compatible solutes in the present compositions serve to both stimulate or maintain uptake of these protective substances into the corneal surface cells, and to provide abundant supplies of these materials or substances.

In addition to sufficient quantities of compatible solutes in a supra-tonic medium, the present compositions also may contain appropriate demulcents and viscosity agents, which provide comfort and lubrication, and also advantageously are effective in holding the organic compatible solute composition on the ocular surface for sufficient time to enhance uptake by the corneal surface cells.

It should be noted that FDA guidelines clearly indicate that the final tonicity of the formulation may be determined by nonionic as well as ionic species. Thus, the formula may contain significant amounts of glycerol and other compatible solutes, and not contain substantial amounts or any of ionic tonicity agents, such as sodium salts. In one embodiment, the present components are substantially free of ionic tonicity agents.

Advantageously, the present compositions include a combination of different organic compatible solute agents effective to provide for uptake by corneal cells during the time of exposure to the drop during use, for example, about 5 to about 30 minutes, depending on viscosity, after administration, and to provide for intracellular retention during the period of hours between drop applications.

Because of the enhanced protection from osmotic insult provided by the present composition, the duration of clinical benefit resulting from each dosage or application is increased. With regular use of the present compositions, ocular surface health is enhanced as cells are less metabolically challenged and cell survival is enhanced.

Another aspect of the present invention, compositions comprising a carrier component and a polyanionic component are provided. Such polyanionic component-containing compositions advantageously, although in certain embodiments not necessarily, include organic compatible solute components as described herein.

In one embodiment, compositions are provided which comprise a carrier component and a polyanionic component in an amount effective to treat an ocular surface of an eye under a condition of an increased population of cationic species, for example and without limitation, increased Major Basic Protein (MBP), and/or decreased polyanionic species on the surface. In one embodiment, the present ophthalmic compositions include polyanionic components present in amounts effective, when the compositions are administered to human or animal eyes, to reduce at least one adverse effect of a cationic, e.g., polycationic, material on an ocular surface relative to an identical composition without the polyanionic component.

In one useful embodiment, compositions comprising polyanionic components, for example, with or without the compatible solute components, may be effectively used before, during and/or after surgical procedures, including without limitation, surgical procedures in which the eye is exposed to laser energy, for example, in the treatment of post-LASIK staining, dryness and other ocular surface complications. The etiology of post-LASIK surface compromise may be multifactorial, including, without limitation, surgically-induced neurotrophic hypesthesia and keratitis, damage to limbal cells from force of the suction ring, altered lid apposition in blinking due to altered corneal topography, chemical damage to ocular surface from topical medications and preservatives and the like.

The administration of polyanionic component-containing compositions, in accordance with the present invention, to the ocular surface and tear film may be effective in treating one or more or even all, of the above named causes of post-LASIK ocular surface compromise.

In one particularly useful embodiment, the present compositions include polyanionic components that mimic the activity, for example, the antigenic and/or cytotoxic activity, of the pro-piece of MBP, which has been shown to consist of a 90-residue polypeptide. Useful agents may include one or more polypeptide analogs of this sequence or portions of this sequence.

As used herein, the term "mimic" means that the polyanionic component, e.g., polypeptide analog, has an activity within (plus or minus) about 5% or about 10% or about 15% or about 20% of the corresponding activity of the pro-piece of MBP.

The pro-piece of MBP has an amino acid sequence as shown in SEQ ID NO:1 below:

Ihlrsetstf etplgaktlp edeetpeqem eetperelee eeewgsgsed askkdgaves isvpdmvdkn ltcpeeedtv kvvgipgcq A polypeptide analog of the Major Basic Protein pro-piece sequence or of a portion of the Major Basic Protein pro-piece sequence means a peptide comprising an amino acid sequence having at least about 75% or about 80% or about 85% or about 90% or about 95% or about 99% or more identity to a homologous continuous amino acid sequence comprised in SEQ ID NO:1, or portions thereof.

Carboxymethyl-substituted polymers of sugars, for example and without limitation, glucose and the like sugars, may be employed as polyanionic components in accordance with the present invention.

Further, additional useful polyanionic components include, without limitation, modified carbohydrates, other polyanionic polymers, for example, and without limitation, those already available for pharmaceutical use, and mixtures thereof. Mixtures of one or more of the above-noted polypeptide analogs and one or more of the above-noted other polyanionic components may be employed.

The present compositions are advantageously ophthalmically acceptable, comprising an ophthalmically acceptable carrier component, a compatible solute component and/or a polyanionic component.

A composition, carrier component or other component or material is "ophthalmically acceptable" when it is compatible with ocular tissue, that is, it does not cause significant or undue detrimental effects when brought into contact with ocular tissue. Preferably, the ophthalmically acceptable component or material is also compatible with other components of the present compositions.

As used herein, the term "polyanionic component" refers to a chemical entity, for example, an ionically charged species, such as an ionically charged polymeric material, which includes more than one discrete anionic charge, that is multiple discrete anionic charges. Preferably, the polyanionic component is selected from the group consisting of polymeric materials having multiple anionic charges and mixtures thereof.

The polyanionic component may have a substantially constant or uniform molecular weight, or may be made up of two or more polyanionic component portions of different molecular weights. Ophthalmic compositions having polyanionic components including two or more portions of different molecular weights are disclosed in U.S. patent application Ser. No. 10/017,817, filed Dec. 14, 2001, the disclosure of which is hereby incorporated in its entirety herein by reference.

Preferably, the composition has an increased ability to adhere to an eye when the composition is administered to an eye relative to a substantially identical composition without the polyanionic component. With regard to the increased ability to adhere to an eye feature noted above, the present compositions preferably are effective to provide effective lubrication over a longer period of time before requiring readministration relative to a substantially identical composition without the polyanionic component.

Any suitable polyanionic component may be employed in accordance with the present invention provided that it functions as described herein and has no substantial detrimental effect on the composition as a whole or on the eye to which the composition is administered. The polyanionic component is preferably ophthalmically acceptable at the concentrations used. The polyanionic component preferably includes three (3) or more anionic (or negative) charges. In the event that the polyanionic component is a polymeric material, it is preferred that many of the repeating units of the polymeric material include a discrete anionic charge. Particularly useful anionic components are those which are water soluble, for example, soluble at the concentrations used in the present compositions at ambient (room) temperature.

Examples of suitable polyanionic components useful in the present compositions include, without limitation, anionic cellulose derivatives, anionic acrylic acid-containing polymers, anionic methacrylic acid-containing polymers, anionic amino acid-containing polymers and mixtures thereof. Anionic cellulose derivatives are very useful in the present invention.

A particularly useful class of polyanionic components are one or more polymeric materials having multiple anionic charges. Examples include, but are not limited to:

metal carboxy methylcelluloses
metal carboxy methylhydroxyethylcelluloses
metal carboxy methylstarches
metal carboxy methylhydroxyethylstarches
metal carboxy methylpropyl guars
hydrolyzed polyacrylam ides and polyacrylonitriles
heparin
glycoam inoglycans
hyaluronic acid
chondroitin sulfate
dermatan sulfate
peptides and polypeptides
alginic acid
metal alginates
homopolymers and copolymers of one or more of:
acrylic and methacrylic acids
metal acrylates and methacrylates
vinylsulfonic acid
metal vinylsulfonate
amino acids, such as aspartic acid, glutamic acid and the like
metal salts of amino acids
p-styrenesulfonic acid
metal p-styrenesulfonate
2-methacryloyloxyethylsulfonic acids
metal 2-methacryloyloxethylsulfonates
3-methacryloyloxy-2-hydroxypropylsulfonic acids
metal 3-methacryloyloxy-2-hydroxypropylsulfonates
2-acrylamido-2-methylpropanesulfonic acids
metal 2-acrylamido-2-methylpropanesulfonates
allylsulfonic acid
metal allylsulfonate and the like.

Excellent results are achieved using polyanionic components selected from carboxy methylcelluloses and mixtures thereof, for example, alkali metal and/or alkaline earth metal carboxy methylcelluloses.

The present compositions preferably are solutions, although other forms, such as ointments, gels, and the like, may be employed.

The carrier component is ophthalmically acceptable and may include one or more components which are effective in providing such ophthalmic acceptability and/or otherwise benefiting the composition and/or the eye to which the composition is administered and/or the patient whose eye is being treated. Advantageously, the carrier component is aqueous-based, for example, comprising a major amount that is at least about 50% by weight, of water. Other components which may be included in the carrier components include, without limitation, buffer components, tonicity components, preservative components, pH adjustors, components commonly found in artificial tears and the like and mixtures thereof.

The present compositions preferably have viscosities in excess of the viscosity of water. In one embodiment, the viscosity of the present compositions is at least about 10 cps (centipoise), more preferably in a range of about 10 cps to about 500 cps or about 1,000 cps. Advantageously, the viscosity of the present composition is in a range of about 15 cps or about 30 cps or about 70 to about 150 cps or about 200 cps or about 300 cps or about 500 cps. The viscosity of the present composition may be measured in any suitable, for example, conventional manner. A conventional Brookfield viscometer measures such viscosities.

In one very useful embodiment, the polyanionic component is present in an amount in a range of about 0.1% to about 5%, preferably about 0.2% to about 2.5%, more preferably about 0.2% to about 1.8% and still more preferably about 0.4% to about 1.3% (w/v) of the composition.

Other components which may be included in the carrier components include, without limitation, buffer components, tonicity components, preservative-components, pH adjustors, components commonly found in artificial tears, such as one or more electrolytes, and the like and mixtures thereof. In one very useful embodiment the carrier component includes at least one of the following: an effective amount of a buffer component; an effective amount of a tonicity component; an effective amount of a preservative component; and water.

These additional components preferably are ophthalmically acceptable and can be chosen from materials which are conventionally employed in ophthalmic compositions, for example, compositions used to treat eyes afflicted with dry eye syndrome, artificial tear formulations and the like.

Acceptable effective concentrations for these additional components in the compositions of the invention are readily apparent to the skilled practitioner.

The carrier component preferably includes an effective amount of a tonicity adjusting component to provide the composition with the desired tonicity. The carrier component preferably includes a buffer component which is present in an amount effective to maintain the pH of the composition in the desired range. Among the suitable tonicity adjusting components that may be employed are those conventionally used in ophthalmic compositions, such as one or more various inorganic salts and the like. Sodium chloride, potassium chloride, mannitol, dextrose, glycerin, propylene glycol and the like and mixtures thereof are very useful tonicity adjusting components. Among the suitable buffer components or buffering agents that may be employed are those conventionally used in ophthalmic compositions. The buffer salts include alkali metal, alkaline earth metal and/or ammonium salts, as well as citrate, phosphate, borate, lactate and the like salts and mixtures thereof. Conventional organic buffers, such as Goode's buffer and the like, may also be employed.

Any suitable preservative component may be included in the present compositions provided that such components is effective as a preservative in the presence of the polyanionic component. Thus, it is important that the preservative component be substantially unaffected by the presence of the polyanionic component. Of course, the preservative component chosen depends on various factors, for example, the specific polyanionic component present, the other components present in the composition, etc. Examples of the useful preservative components include, but are not limited to, per-salts, such as perborates, percarbonates and the like; peroxides, such as very low concentrations, e.g., about 50 to about 200 ppm (w/v), of hydrogen peroxide and the like; alcohols, such as benzyl alcohol, chlorobutanol and like; sorbic acid and ophthalmically acceptable salts thereof and mixtures thereof.

The amount of preservative component included in the present compositions containing such a component varies over a relatively wide range depending, for example, on the specific preservative component employed. The amount of such component preferably is in the range of about 0.000001% to about 0.05% or more (w/v) of the present composition.

One particularly useful class of preservative components are chlorine dioxide precursors. Specific examples of chlorine dioxide precursors include stabilized chlorine dioxide (SCD), metal chlorites, such as alkali metal and alkaline earth metal chlorites, and the like and mixtures thereof. Technical grade sodium chlorite is a very useful chlorine dioxide precursor. Chlorine dioxide-containing complexes, such as complexes of chlorine dioxide with carbonate, chlorine dioxide with bicarbonate and mixtures thereof are also included as chlorine dioxide precursors. The exact chemical composition of many chlorine dioxide precursors, for example, SCD and the chlorine dioxide complexes, is not completely understood. The manufacture or production of certain chlorine dioxide precursors is described in McNicholas U.S. Pat. No. 3,278,447, which is incorporated in its entirety herein by reference. Specific examples of useful SCD products include that sold under the trademark Purite® by Allergan, Inc., that sold under the trademark Dura Klor by Rio Linda Chemical Company, Inc., and that sold under the trademark Anthium Dioxide by International Dioxide, Inc.

The chlorine dioxide precursor is included in the present compositions to effectively preserve the compositions. Such effective preserving concentrations preferably are in the range of about 0.0002 or about 0.002 to about 0.02% (w/v) or higher of the present compositions.

In the event that chlorine dioxide precursors are employed as preservative components, the compositions preferably have an osmolality of at least about 200 mOsmol/kg and are buffered to maintain the pH within an acceptable physiological range, for example, a range of about 6 to about 8 or about 10.

The present compositions preferably include an effective amount of an electrolyte component, that is one or more electrolytes, for example, such as is found in natural tears and artificial tear formulations. Examples of particularly useful such electrolytes for inclusion in the present compositions include, without limitation, alkaline earth metal salts, such as alkaline earth metal inorganic salts, and mixtures thereof, e.g., calcium salts, magnesium salts and mixtures thereof. Very good results are obtained using an electrolyte component selected from calcium chloride, magnesium chloride and mixtures thereof.

The amount or concentration of such electrolyte component in the present compositions can vary widely and depends on various factors, for example, the specific electrolyte component being employed, the specific composition in which the electrolyte is to be included and the like factors. In one useful embodiment, the amount of the electrolyte component is chosen to at least partially resemble, or even substantially resemble, the electrolyte concentration in natural human tears. Preferably, the concentration of the electrolyte component is in the range of about 0.01 to about 0.5 or about 1% of the present composition.

The present compositions may be prepared using conventional procedures and techniques. For example, the present compositions can be prepared by blending the components together, such as in one bulk.

To illustrate, in one embodiment, the polyanionic component portions are combined with purified water and caused to disperse in the purified water, for example, by mixing and/or agitation. The other components, such as the buffer component, tonicity component, electrolyte component, preservative component and the like, are introduced as the mixing continues. The final mixture is sterilized, such as steam sterilized, for example, at temperatures of at least about 100° C., such as in a range of about 120° C. to about 130° C., for a time of at least about 15 minutes or at least about 30 minutes, such as in a range of about 45 to about 60 minutes. In one embodiment, the preservative component preferably is added to the mixture after sterilization. The final product preferably is filtered, for example, through a 20 micron sterilized cartridge filter, such as a 20 micron clarity filter cartridge, e.g., sold by Pall under the tradename HDC II, to provide a clear, smooth solution, which is then aseptically filled into containers, for example, low density polyethylene teal containers.

Alternately, each of the polyanionic component portions can be mixed with purified water to obtain individual polyanionic component portion solutions. By mixing the individual polyanionic component portion solutions together, a blend is easily and effectively obtained having the desired, controlled ratio of the individual polyanionic component portions. The blended solution can then be combined with the other components, sterilized and filled into containers, as noted above.

In one particularly useful embodiment, a solution of the polyanionic component portions and purified water is obtained, as noted above. This solution is then sterilized, for example, as noted above. Separately, the other components to be included in the final composition are solubilized in purified water. This latter solution is sterile filtered, for example, through a 0.2 micron sterilizing filter, such as that sold by Pall under the tradename Suporflow, into the polyanionic component-containing solution to form the final solution. The final solution is filtered, for example, as noted above, to provide a clear, smooth solution which is then aseptically filled into containers, as noted above.

The present compositions may be effectively used, as needed, by methods which comprise administering an effective amount of the composition to an eye in need of lubrication, for example, an eye afflicted with dry eye syndrome or having a propensity toward dry eye syndrome. The administering step may be repeated as needed to provide effective lubrication to such eye. The mode of administration of the present composition depends on the form of the composition. For example, if the composition is a solution, drops of the composition may be applied to the eye, e.g., from a conventional eye dropper. In general, the present compositions may be applied to the surface of the eye in substantially the same way as conventional ophthalmic compositions are applied. Such administration of the present compositions does provide substantial and unexpected benefits, as described elsewhere herein.

The following non-limiting examples illustrate certain aspects of the present invention.

EXAMPLE 1

In this experiment, corneal epithelial cells were isolated from the rabbit eye and grown under conditions so that they differentiate into a layered "air-lift" culture that includes basal, wing, and squamous cells. As they grow and differentiate, these cultures developed tight junctions between cells that provide the basis for a trans-epithelial electrical resistance (TEER) across the cell layers between the apical and basal surfaces. The TEER value is a sensitive measure of cell growth, differentiation and health.

After 5 days in culture during which the layered structure forms, different culture wells were exposed to hypertonic fluid (400 mOsmols/kg) with or without addition of one of 6 candidate compatible solutes at a low concentration (2 mM). The TEER was then measured after 22 hours of exposure. The TEER value was expressed as a percentage of the TEER value obtained from a similar culture under isotonic (300 mOsmol/kg) conditions. The results of these tests are shown in Table 1.

TABLE 1

| Test Results | |
|---|---|
| Compatible Solute | TEER (as % of isotonic control) at 22 hours |
| Isotonic Control | 100% |
| Hypertonic Control | 23.3 |
| 2 mM Taurine | 39.8 |
| 2 mM Betaine | 53.3 |
| 2 mM Carnitine | 118.9 |
| 2 mM Erythritol | 107.4 |
| 2 mM Myo-Inositol | 74.8 |
| 2 mM Xylitol | 94.1 |

These results demonstrate that all of the candidates tested have some osmoprotective ability, increasing the TEER relative to the hypertonic control. Surprisingly, of the agents tested, carnitine produced the most benefit. Without wishing to limit the invention to any particular theory of operation, it is believed that the beneficial results obtained with carnitine may relate to carnitine's multiple roles in energy metabolism and other cellular mechanisms as well as its osmoprotective effects.

Further, and also unexpectedly, erythritol provided the best results among the polyols tested. Xylitol and myo-inositol provided good results.

These results indicate that each of the 6 candidate compounds, and preferably, carnitine, erythritol, xylitol and myo-inositol, may be useful in ophthalmic compositions, for example, to mitigate against hypertonic conditions on ocular surfaces of human or animal eyes.

Again, without wishing to limit the invention to any particular theory of operation, it is believed that, due to the varying roles a number of these compounds may play, that combinations of 2 or more of these compounds, for example, including at least one polyol and at least one amino acid, are likely to provide increased protection of corneal surfaces from insults, for example, due to desiccation and hyperosmolality, such as occur in dry eye disease.

EXAMPLE 2

Phosphorylated JNK (the activated form of the stress associated protein kinase, SAPK) plays a key role in induction of inflammation and apoptosis in response to stress, including hyperosmolarity.

Human corneoscleral tissues, from donors aged 16-59 years were obtained from the Lions Eye Bank of Texas (Houston, Tex.). Corneal epithelial cells were grown from limbal explants. In brief, after carefully removing the central cornea, excess conjunctiva and iris and corneal endothelium, the limbal rim was cut into 12 equal pieces (about 2×2 mm size each). Two of these pieces were placed epithelial side up into each well of 6-well culture plates, and each explant was covered with a drop of fetal bovine serum (FBS) overnight. The explants were then cultured in SHEM medium, which was an 1:1 mixture of Dulbecco modified Eagle medium (DMEM) and Ham F-12 medium containing 5 ng/mL EGF, 5 µg/mL insulin, 5 µg/mL transferrin, 5 ng/mL sodium selenite, 0.5 µg/mL hydrocortisone, 30 ng/mL cholera toxin A, 0.5% DMSO, 50 µg/mL gentamicin, 1.25 µg/mL amphotericin B and 5% FBS, at 37° C. under 5% $CO_2$ and 95% humidity. The medium was renewed every 2-3 days. Epithelial phenotype of these cultures was confirmed by characteristic morphology and immuno-fluorescent staining with cytokeratin antibodies (AE-1/AE-3).

Cell culture dishes, plates, centrifuge tubes and other plastic ware were purchased from Becton Dickinson (Lincoln Park, N.J.). Dulbecco modified Eagle medium (DMEM), Ham F-12 medium, Fungizone, and gentamicin were from Invitrogen-GIBCO BRL (Grand Island, N.Y.). Fetal bovine serum (FBS) was from Hyclone (Logan, Utah).

A series of primary sub-confluent corneal epithelial cultures (grown for 12 to 14 days, about 4-5×10$^5$ cells/well) were washed three times with preserved buffered saline (PBS) and switched to an Earle's Balanced Salt Solution (EBSS, 300 mOsmols/kg) for 24 hours before treatment. The corneal epithelial cells were cultured for 1 hour in an equal volume (2.0 mL/well) of EBSS media or 400 mOsmols/kg media by adding 53 mM NaCl or sucrose, with either L-carnitine inner salt, betaine hydrochloride, erythritol, or xylitol (all at a concentration of 2 mM) that were pre-added 60 minutes before adding NaCl or sucrose. Samples without these osmoprotectants were also prepared and tested.

The adherent cells were lysed in Beadlyte® Buffer B (included in the Beadlyte® Cell Signaling buffer kit, Upstate Biotechnology, Lake Placid, N.Y.) containing an EDTA-free protease inhibitor cocktail tablet (Roche Applied Science, Indianapolis, Ind.) for 15 minutes. The cell extracts were centrifuged at 12,000×g for 15 minutes at room temperature and the supernatants were stored at −80° C. until they were analyzed by Western blot analysis. The total protein concentrations of the cell extracts were determined using a Micro BCA protein assay kit (Pierce, Rockford, Ill.).

The intensity of each of JNK1 and JNK2 was tested for each of these compositions using Western blot analysis with specific antibodies to each phosphorylated species.

The Western blot analysis was conducted as follows. The protein samples (50 µg per lane) were mixed with 6×SDS reducing sample buffer and boiled for 5 minutes before loading. Proteins were separated by SDS polyacrylamide gel electrophoresis (4-15% Tris-HCl, gradient gels from Bio-Rad, Hercules, Calif.), and transferred electronically to polyvinylidene difluoride (PVDF) membranes (Millipore, Bedford, Mass.). The membranes were blocked with 5% non-fat milk in TTBS (50 mM Tris, pH 7.5, 0.9% NaCl, and 0.1% Tween-20) for 1 hour at room temperature (RT), and then incubated 2 hours at RT with a 1:1000 dilution of rabbit antibody against phospho-p38 MAPK (Cell Signaling, Beverly, Mass.), 1:100 dilution of rabbit antibody against phospho-JNK, or 1:500 dilution of monoclonal antibody against phospho-p44/42 ERK (Santa Cruz Biotechnology, Santa Cruz, Calif.).

After three washings with TTBS, the membranes were incubated for 1 hour at RT with horseradish peroxidase-conjugated secondary antibody goat anti-rabbit IgG (1:2000 dilution, Cell Signaling, Beverly, Mass.), or goat anti-mouse IgG (1:5000 dilution, Pierce, Rockford, Ill.). After washing the membranes four times, the signals were detected with an ECL advance chemiluminescence reagent (Amersham, Piscataway, N.J.) and the images were acquired by a Kodak image station 2000R (Eastman Kodak, New Haven, Conn.). The membranes were stripped in 62.5 mM Tris HCl, pH 6.8, containing 2% SDS and 100 mM α-mercaptoethanol at 60° C. for 30 minutes, then they were re-probed with 1:100 dilution of rabbit antibody against JNK (Santa Cruz Biotechnology) or 1:1000 dilution of rabbit antibodies against ERK or p38 MAPK (Cell Signaling). These three antibodies detect both phosphorylated and un-phosphorylated forms which represent the total levels of these MAPKs. The signals were detected and captured as described above.

An intensity score is determined from image analysis of the resulting bands.

Figure 2:
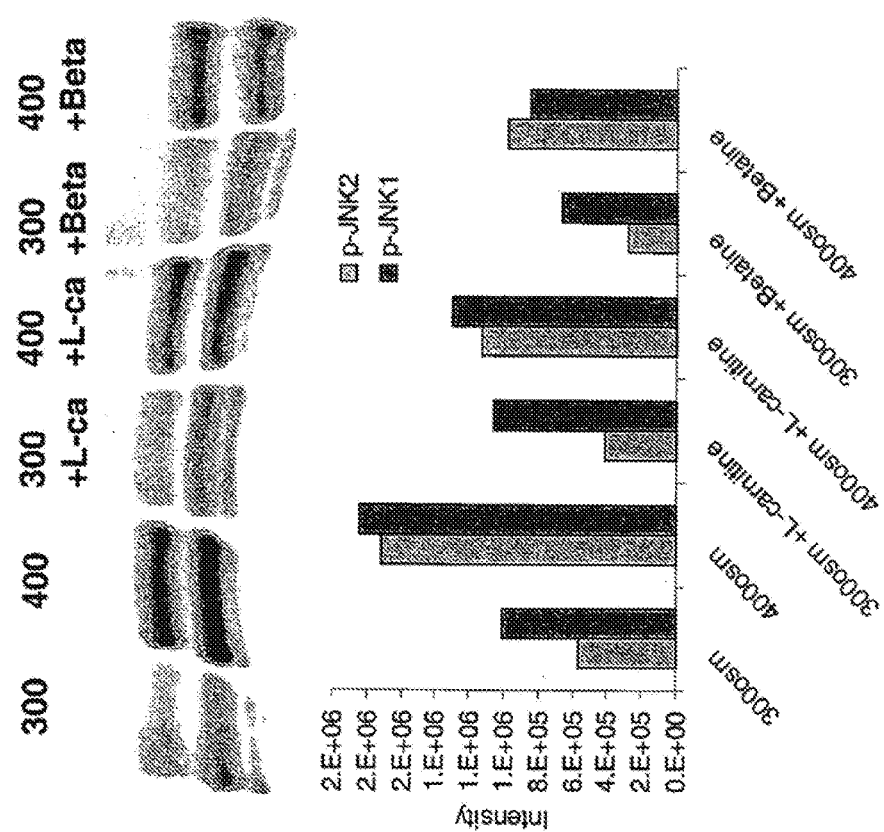
FIG. 2 is a graphical presentation of the intensity with regard to p-JNK1 and p-JNK2 of certain other ophthalmic compositions.

Test results are shown in FIGS. 1 and 2.

Referring now to FIG. 1, there was no effect on JNK activation with either erythritol or xylitol. However, with reference to FIG. 2, there was a definite decrease in the levels of JNK1 and JNK2 in L-carnitine and betaine cultures compared to 400 mOsmols/kg media alone. There was also a less robust effect in the 300 mOsmols/kg cultures.

EXAMPLE 3

In another series of experiments, the Beadlyte® Cell Signaling Assay was used. This assay is a fluorescent bead-based sandwich immunoassay. Each sample (10 µg/25 µL) was pipetted into a well of a 96-well plate and incubated with 25 µL of diluted 5×beads coupled to phospho-JNK, phospho-ERK, phospho-p38 or total JNK, or total ERK, or total p38 specific capture antibodies overnight. Overnight incubation was utilized for the reaction of the capture beads with the proteins from the cell lysates.

The beads were washed and mixed with biotinylated specific reporter antibodies for phospho-MAPK or total-MAPK, followed by streptavidin-phycoerythrin. The amount of total or phospho-MAPK was then quantified by the Luminex 100™ system (Luminex, Austin, Tex.). Fifty events per bead were read, and the data output obtained from the Bio-Plex Manager software were exported to Microsoft Excel® for further analysis. The results were presented as the percentage of phospho-MAPK to total-MAPK.

Figure 3:
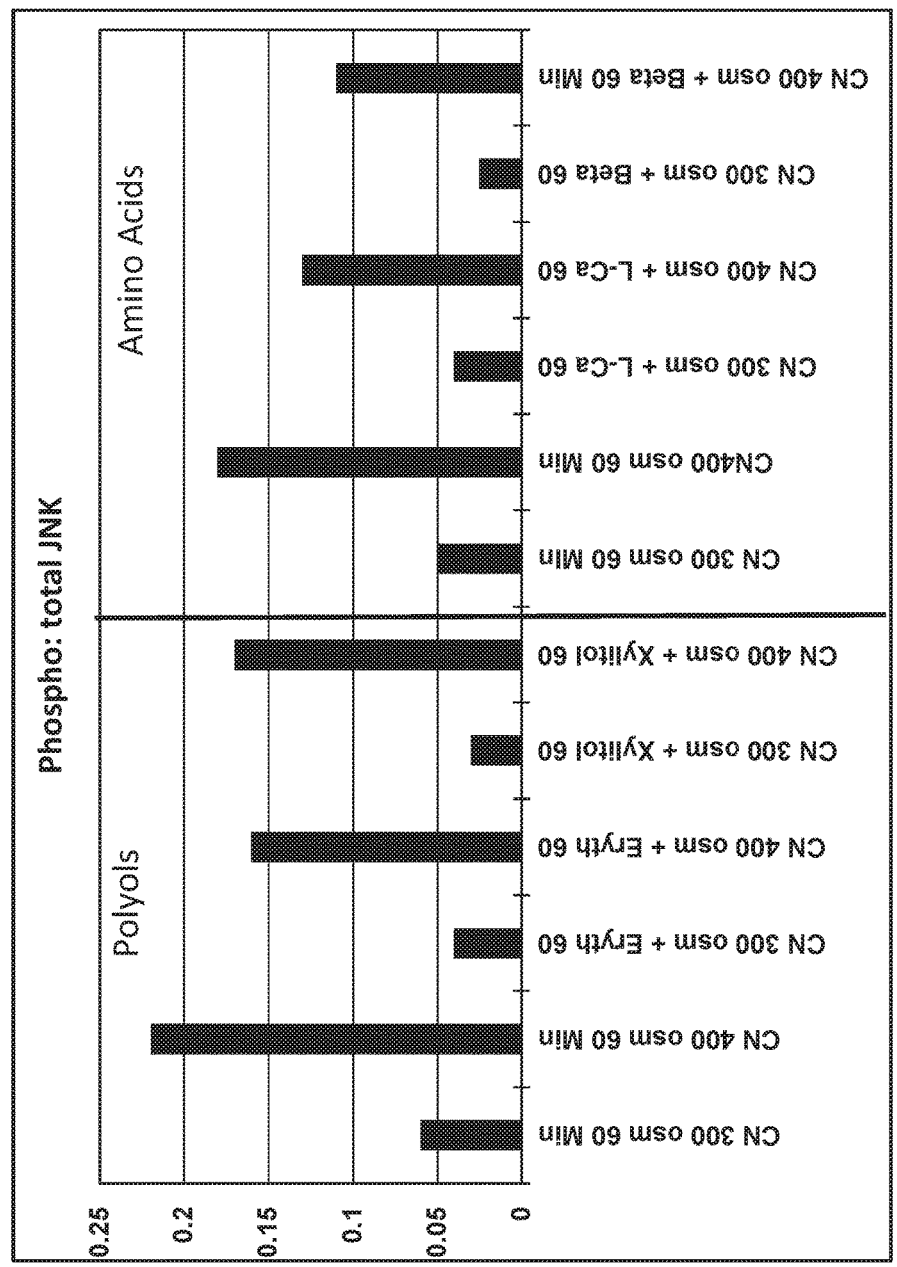
FIG. 3 is a graphical presentation of Phosphorylated:total JNK ratios for certain ophthalmic compositions obtained using the Beadlyte method.
Figure 4:
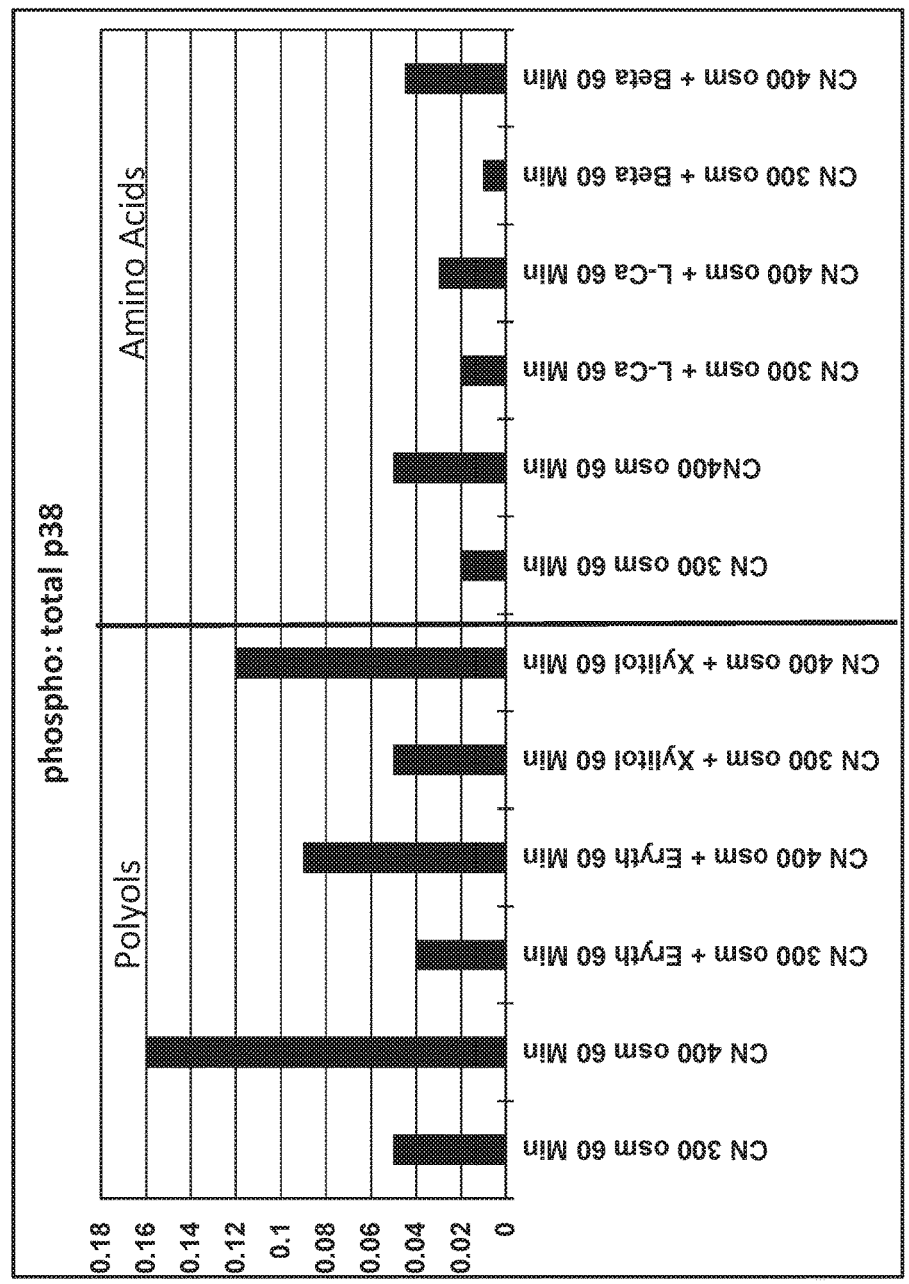
FIG. 4 is a graphical presentation of Phospho:total p38 MAP Kinase for certain ophthalmic compositions obtained using the Beadlyte method.
Figure 5:
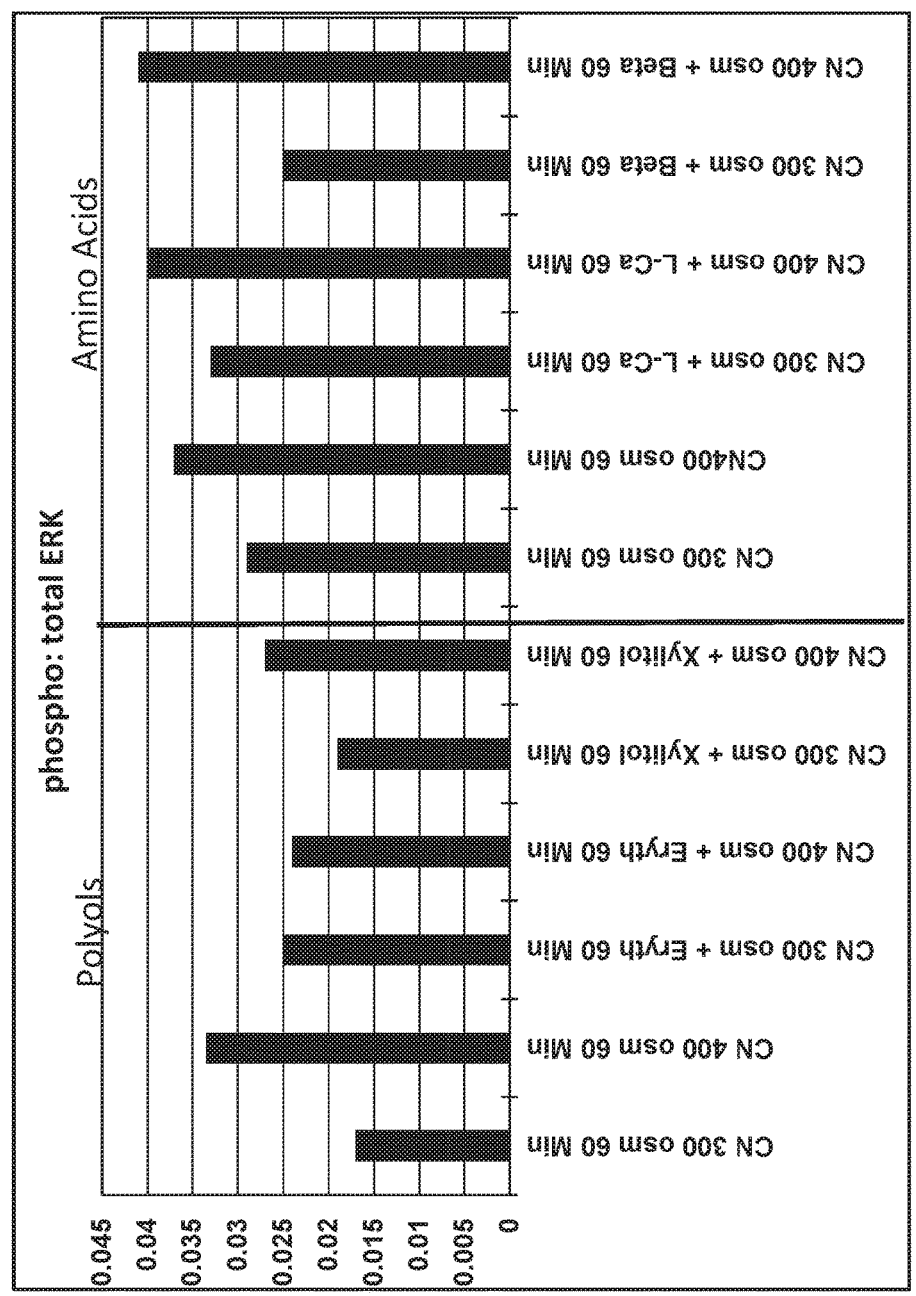
FIG. 5 is a graphical presentation of Phospho:total ERK MAP Kinase for certain ophthalmic compositions obtained using the Beadlyte method.

Results of these tests are shown in FIGS. 3, 4 and 5.

As shown in FIG. 3, all of the candidate materials, that is, all of erythritol, xylitol, L-carnitine and betaine, reduced the amount of phospho-total JNK relative to the hypertonic control.

With reference to FIG. 4, all of the candidate materials, with the exception of betaine, reduced the amount of phospho-total p 38 relative to the hypertonic control.

As shown in FIG. 5, the polyol candidate materials, that is erythritol and xylitol reduced the amount of ERK relative to the hypertonic control. The amino acids, betaine and carnitine did not.

EXAMPLE 4

Example 1 is repeated except that different concentrations of each of the candidate materials are used, and the TEER is measured at various times from 0 to 24 hours.

Figure 6:
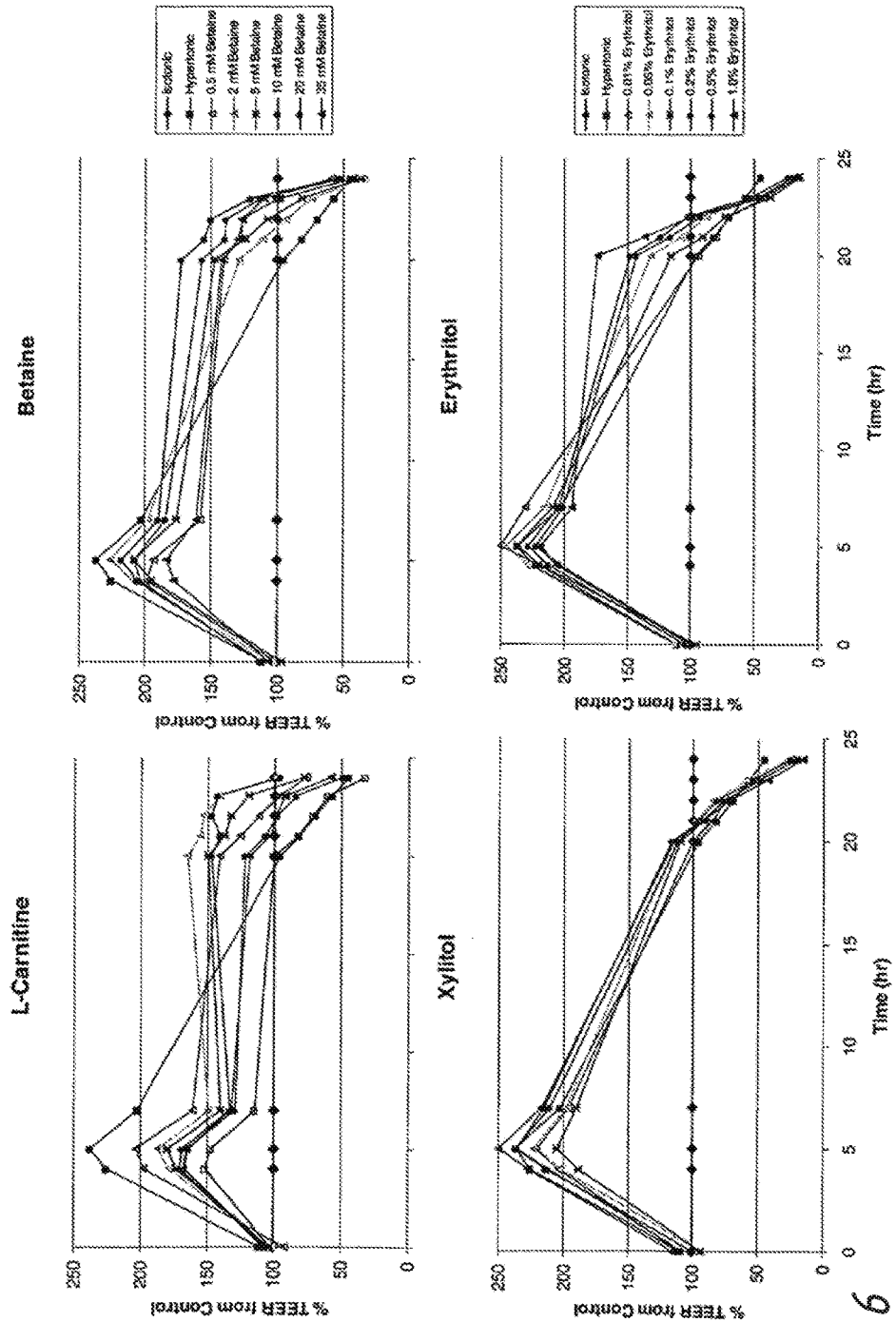
FIG. 6 is a graphical presentation of a summary of concentration dependent effects on trans-epithelial electrical resistance (TEER) for various ophthalmic compositions.

Results of these tests are shown in FIG. 6. As in Example 1, the TEER variable is represented as % TEER relative to the isotonic control.

These results demonstrate that a dose-related response was observed for L-carnitine, betaine and erythritol.

A composition including betaine and stabilized chlorine dioxide, as a preservative, was tested for component compatibility. It was found that the betaine was not fully compatible in such a composition. Thus, betaine is not useful with certain preservatives, such as stabilized chlorine dioxide. However, betaine may advantageously be employed as a compatible solute in ophthalmic compositions which use other preservative systems, or which are free of preservatives, for example, in single or unit-dose applications.

EXAMPLE 5

Example 4 was repeated except that compositions including combinations of compatible solutes were used. Compositions including only glycerol as a compatible solute were also tested.

Figure 7:
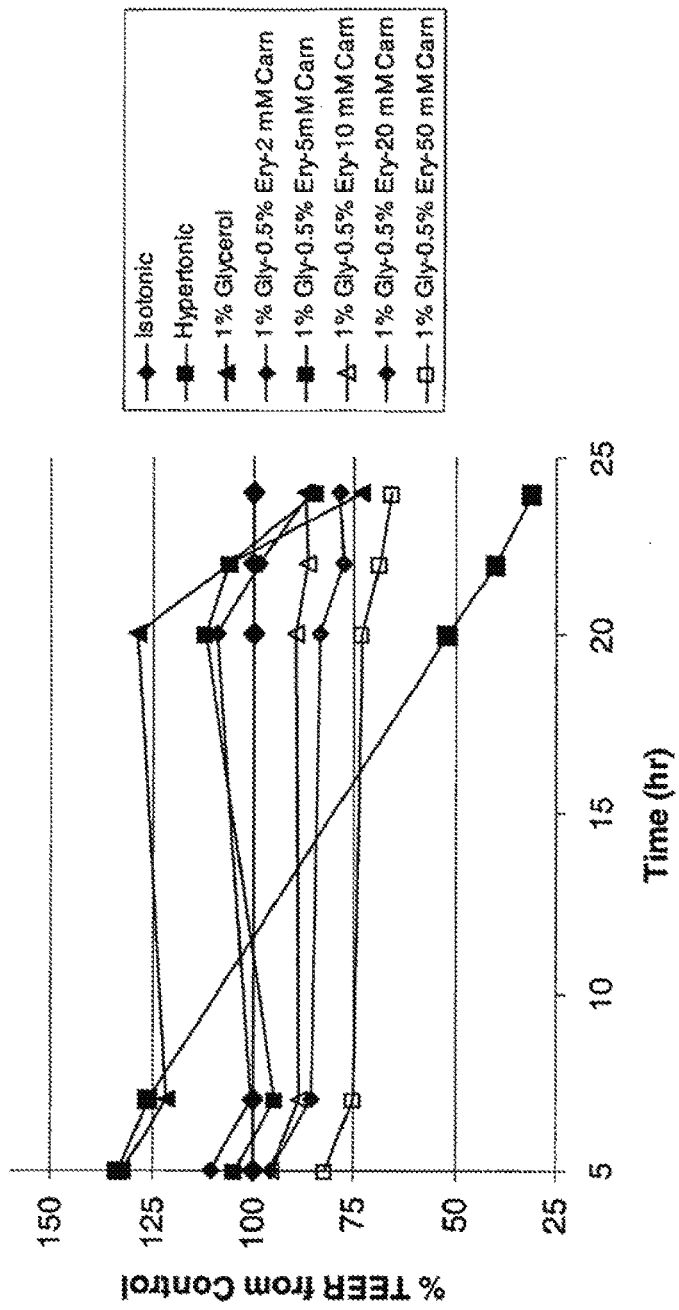
FIG. 7 is a graphical presentation of the effects on TEER of various ophthalmic compositions including compositions including combinations of compatible solute agents.
Figure 8:
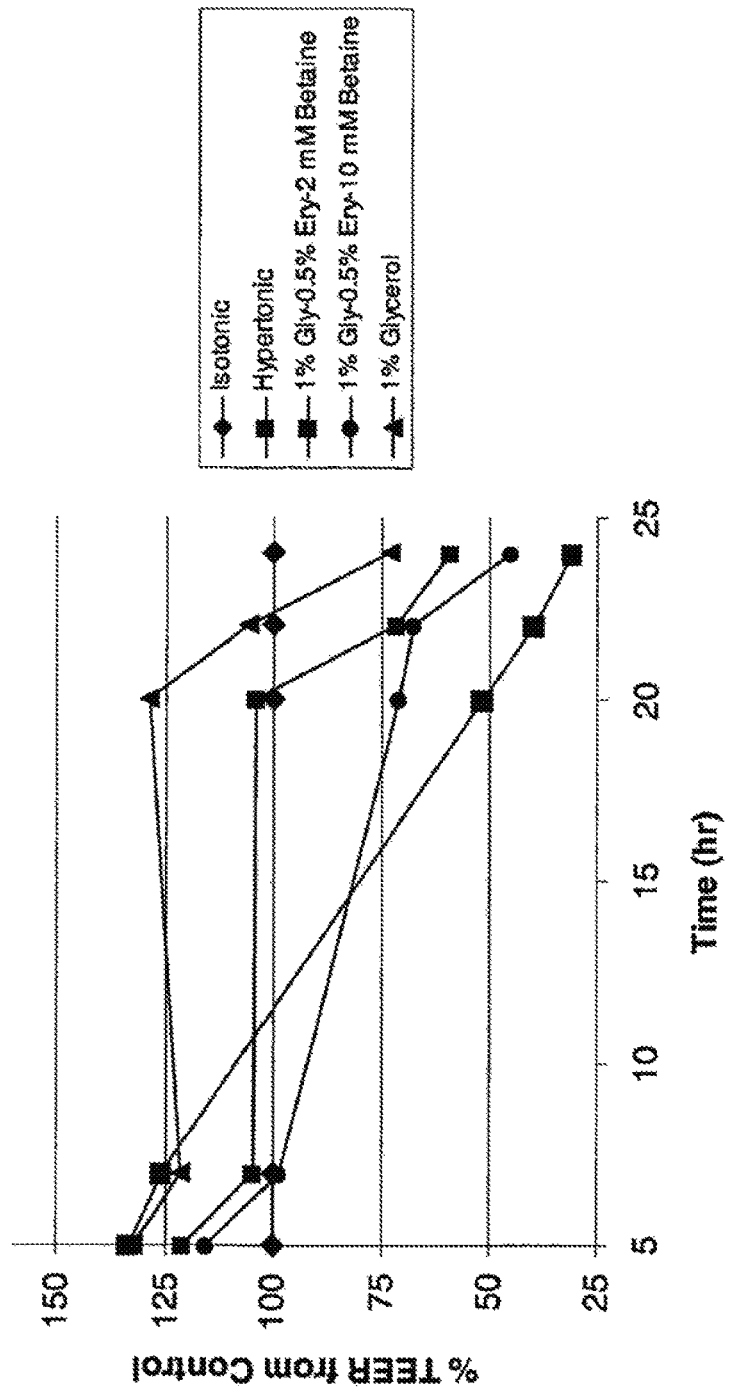
FIG. 8 is a graphical presentation of the effects on TEER of various other ophthalmic compositions including compositions including combinations of compatible solute agents.

Test results are shown in FIGS. 7 and 8.

These test results demonstrate that combinations of different compatible solutes may potentially yield added benefits.

EXAMPLE 6

The pro-piece of Major Basic Protein (MBP) has been shown to be a 90-residue polypeptide.

Using established and well known techniques, a polypeptide analog of the sequence of this 90-residue polypeptide is produced.

An ophthalmic composition is prepared by blending together the following components:

|  | Concentration % (w/v) |
|---|---|
| Above-noted Polypeptide analog | 0.5% |
| Glycerol | 1.0% |
| Erythritol | 0.5% |
| Boric Acid | 0.65 |
| Sodium Borate | 0.25 |
| Sodium Citrate | 0.1 |
| Potassium Chloride | 0.01 |
| Purite ®[(1)] | 0.01 |
| Sodium Hydroxide 1N | Adjust pH to 7.2 |
| Hydrochloride acid 1N | Adjust pH to 7.2 |
| Purified Water | q.s. ad. |

[(1)]Purite ® is a registered trademark of Allergan, Inc. for stabilized chlorine dioxide. This material is added to the mixture after heat sterilization.

EXAMPLE 7

The composition of Example 6, in the form of eye drops, is administered to the eye of a human patient about to undergo a surgical procedure in which the eye is to be exposed to laser energy, in particular, a LASIK surgical procedure.

After the surgical procedure, the patient has reduced pain and/or reduced discomfort and/or reduced eye irritation and/or more rapid recovery from the surgical procedure relative to undergoing an identical surgical procedure including being administered the same composition without the polypeptide analog.

EXAMPLE 8

The composition of Example 6, in the form of eye drops, is administered to the eye of a human patient undergoing a surgical procedure in which the eye is to be exposed to laser energy, in particular, a LASIK surgical procedure.

After the surgical procedure, the patient has reduced pain and/or reduced discomfort and/or reduced eye irritation and/or more rapid recovery from the surgical procedure relative to undergoing an identical surgical procedure including being administered the same composition without the polypeptide analog.

EXAMPLE 9

The composition of Example 6, in the form of eye drops, is administered to the eye of a human patient substantially immediately after undergoing a surgical procedure in which the eye is to be exposed to laser energy, in particular, a LASIK surgical procedure.

The patient has reduced pain and/or reduced discomfort and/or reduced eye irritation and/or more rapid recovery from the surgical procedure relative to undergoing an identical surgical procedure including being administered the same composition without the polypeptide analog.

EXAMPLE 10

A series of four ophthalmic formulations in accordance with the present invention are prepared by blending the various components (shown in the following table) together.

|  | Concentration, % (w/v) | | | |
|---|---|---|---|---|
| Ingredient | A | B | C | D |
| Carboxy Methylcellulose (CMC) | 1.0 | — | — | 0.5 |
| Glycerol | 0.5 | 0.5 | — | 0.5 |
| Erythritol | 0.25 | 0.25 | 0.75 | 0.75 |
| Boric Acid | 0.60 | 0.60 | 0.60 | 0.60 |
| Sodium Borate Decahydrate | 0.045 | 0.045 | 0.045 | 0.045 |
| Calcium Chloride Dihydrate | 0.006 | 0.006 | 0.006 | 0.006 |
| Magnesium Chloride Hexahydrate | 0.006 | 0.006 | 0.006 | 0.006 |
| Purite ®[(1)] | 0.0075 | 0.0075 | 0.075 | 0.075 |
| Sodium Hydroxide 1N | Adjust pH to 7.2 | Adjust pH to 7.2 | Adjust pH to 7.2 | Adjust pH to 7.2 |
| Hydrochloric Acid 1N | Adjust pH to 7.2 | Adjust pH to 7.2 | Adjust pH to 7.2 | Adjust pH to 7.2 |
| Purified water | q.s. ad. | q.s. ad. | q.s. ad. | q.s. ad. |

[(1)]Purite ® is a registered trademark of Allergan, Inc. for stabilized chlorine dioxide. This material is added to the mixture after heat sterilization.

EXAMPLE 11

The procedure of Example 10 is repeated to provide the following compositions.

|  | Concentration, % (w/v) | | | |
|---|---|---|---|---|
| Ingredient | A | B | C | D |
| Carboxy Methylcellulose (CMC) | 1.0 | — | — | 0.5 |
| Glycerol | 0.5 | 0.5 | — | 0.5 |
| Xylitol | 0.25 | 0.25 | 0.75 | 0.75 |
| Boric Acid | 0.60 | 0.60 | 0.60 | 0.60 |
| Sodium Borate Decahydrate | 0.045 | 0.045 | 0.045 | 0.045 |
| Calcium Chloride Dihydrate | 0.006 | 0.006 | 0.006 | 0.006 |

EXAMPLE 12

The procedure of Example 10 is repeated to provide the following compositions.

| Ingredient | Concentration, % (w/v) | | | |
|---|---|---|---|---|
| | A | B | C | D |
| Carboxy Methylcellulose (CMC) | 1.0 | — | — | 0.5 |
| Glycerol | 0.5 | 0.5 | — | 0.5 |
| Myo-inositol | 0.25 | 0.25 | 0.75 | 0.75 |
| Boric Acid | 0.60 | 0.60 | 0.60 | 0.60 |
| Sodium Borate Decahydrate | 0.045 | 0.045 | 0.045 | 0.045 |
| Calcium Chloride Dihydrate | 0.006 | 0.006 | 0.006 | 0.006 |
| Magnesium Chloride Hexahydrate | 0.006 | 0.006 | 0.006 | 0.006 |
| Purite ®[1] | 0.0075 | 0.0075 | 0.075 | 0.075 |
| Sodium Hydroxide 1N | Adjust pH to 7.2 | Adjust pH to 7.2 | Adjust pH to 7.2 | Adjust pH to 7.2 |
| Hydrochloric Acid 1N | Adjust pH to 7.2 | Adjust pH to 7.2 | Adjust pH to 7.2 | Adjust pH to 7.2 |
| Purified water | q.s. ad. | q.s. ad. | q.s. ad. | q.s. ad. |

[1]Purite ® is a registered trademark of Allergan, Inc. for stabilized chlorine dioxide. This material is added to the mixture after heat sterilization.

(Preceding continued table from page 21 top:)

| Ingredient | Concentration, % (w/v) | | | |
|---|---|---|---|---|
| | A | B | C | D |
| Magnesium Chloride Hexahydrate | 0.006 | 0.006 | 0.006 | 0.006 |
| Purite ®[1] | 0.0075 | 0.0075 | 0.075 | 0.075 |
| Sodium Hydroxide 1N | Adjust pH to 7.2 | Adjust pH to 7.2 | Adjust pH to 7.2 | Adjust pH to 7.2 |
| Hydrochloric Acid 1N | Adjust pH to 7.2 | Adjust pH to 7.2 | Adjust pH to 7.2 | Adjust pH to 7.2 |
| Purified water | q.s. ad. | q.s. ad. | q.s. ad. | q.s. ad. |

[1]Purite ® is a registered trademark of Allergan, Inc. for stabilized chlorine dioxide. This material is added to the mixture after heat sterilization.

EXAMPLE 13

The procedure of Example 10 is repeated to provide the following compositions.

| Ingredient | Concentration, % (w/v) | | | |
|---|---|---|---|---|
| | A | B | C | D |
| Carboxy Methylcellulose (CMC) | 1.0 | — | — | 0.5 |
| Glycerol | 0.5 | 0.5 | — | 0.5 |
| Carnitine | 0.25 | 0.25 | 0.75 | 0.75 |
| Boric Acid | 0.60 | 0.60 | 0.60 | 0.60 |
| Sodium Borate Decahydrate | 0.045 | 0.045 | 0.045 | 0.045 |
| Calcium Chloride Dihydrate | 0.006 | 0.006 | 0.006 | 0.006 |
| Magnesium Chloride Hexahydrate | 0.006 | 0.006 | 0.006 | 0.006 |
| Purite ®[1] | 0.0075 | 0.0075 | 0.075 | 0.075 |
| Sodium Hydroxide 1N | Adjust pH to 7.2 | Adjust pH to 7.2 | Adjust pH to 7.2 | Adjust pH to 7.2 |
| Hydrochloric Acid 1N | Adjust pH to 7.2 | Adjust pH to 7.2 | Adjust pH to 7.2 | Adjust pH to 7.2 |
| Purified water | q.s. ad. | q.s. ad. | q.s. ad. | q.s. ad. |

[1]Purite ® is a registered trademark of Allergan, Inc. for stabilized chlorine dioxide. This material is added to the mixture after heat sterilization.

EXAMPLE 14

The procedure of Example 10 is repeated to provide the following compositions.

| Ingredient | Concentration, % (w/v) | | | |
|---|---|---|---|---|
| | A | B | C | D |
| Carboxy Methylcellulose (CMC) | 1.0 | — | — | 0.5 |
| Glycerol | 0.5 | 0.5 | — | 0.5 |
| Taurine | 0.25 | 0.25 | 0.75 | 0.75 |
| Boric Acid | 0.60 | 0.60 | 0.60 | 0.60 |
| Sodium Borate Decahydrate | 0.045 | 0.045 | 0.045 | 0.045 |
| Calcium Chloride Dihydrate | 0.006 | 0.006 | 0.006 | 0.006 |
| Magnesium Chloride Hexahydrate | 0.006 | 0.006 | 0.006 | 0.006 |
| Purite ®[1] | 0.0075 | 0.0075 | 0.075 | 0.075 |
| Sodium Hydroxide 1N | Adjust pH to 7.2 | Adjust pH to 7.2 | Adjust pH to 7.2 | Adjust pH to 7.2 |
| Hydrochloric Acid 1N | Adjust pH to 7.2 | Adjust pH to 7.2 | Adjust pH to 7.2 | Adjust pH to 7.2 |
| Purified water | q.s. ad. | q.s. ad. | q.s. ad. | q.s. ad. |

[1]Purite ® is a registered trademark of Allergan, Inc. for stabilized chlorine dioxide. This material is added to the mixture after heat sterilization.

EXAMPLE 15

The procedure of Example 10 is repeated to provide the following compositions.

| Ingredient | Concentration, % (w/v) | | | |
|---|---|---|---|---|
| | A | B | C | D |
| Carboxy Methylcellulose (CMC) | 1.0 | — | — | 0.5 |
| Glycerol | 0.5 | 0.5 | — | 0.5 |
| Betaine[2] | 0.25 | 0.25 | 0.75 | 0.75 |
| Boric Acid | 0.60 | 0.60 | 0.60 | 0.60 |
| Sodium Borate Decahydrate | 0.045 | 0.045 | 0.045 | 0.045 |
| Calcium Chloride Dihydrate | 0.006 | 0.006 | 0.006 | 0.006 |
| Magnesium Chloride Hexahydrate | 0.006 | 0.006 | 0.006 | 0.006 |
| Purite ®[1] | 0.0075 | 0.0075 | 0.075 | 0.075 |
| Sodium Hydroxide 1N | Adjust pH to 7.2 | Adjust pH to 7.2 | Adjust pH to 7.2 | Adjust pH to 7.2 |
| Hydrochloric Acid 1N | Adjust pH to 7.2 | Adjust pH to 7.2 | Adjust pH to 7.2 | Adjust pH to 7.2 |
| Purified water | q.s. ad. | q.s. ad. | q.s. ad | q.s. ad. |

[1]Purite ® is a registered trademark of Allergan, Inc. for stabilized chlorine dioxide. This material is added to the mixture after heat sterilization.
[2]Betaine is found to be incompatible with the Purite7 preservative. Therefore, no preservative is used. These compositions are useful in single or unit dose applications.

EXAMPLE 16

The procedure of Example 10 is repeated to provide the following compositions.

| Ingredient | Concentration, % (w/v) | | | |
|---|---|---|---|---|
| | A | B | C | D |
| Carboxy Methylcellulose (CMC) | 0.5 | — | 0.5[3] | — |
| Glycerol | 0.9 | 0.9 | 0.9 | 0.9 |
| Erythritol | 0.5 | 0.5 | 0.25 | 0.25 |

-continued

| Ingredient | Concentration, % (w/v) | | | |
|---|---|---|---|---|
| | A | B | C | D |
| Carnitine HCL | 0.1 | 0.25 | 0.1 | 0.25 |
| Boric Acid | 0.45 | 0.45 | 0.45 | 0.45 |
| Sodium Borate | 0.46 | 0.46 | 0.46 | 0.46 |
| Sodium Citrate | 0.1 | 0.1 | 0.1 | 0.1 |
| Potassium Chloride | 0.14 | 0.14 | 0.14 | 0.14 |
| Calcium Chloride | 0.006 | 0.006 | 0.006 | 0.006 |
| Magnesium Chloride | 0.006 | 0.006 | 0.006 | 0.006 |
| Purite ®[(1)] | 0.01 | 0.01 | 0.01 | 0.01 |
| Sodium Hydroxide 1N | Adjust pH to 7.2 | Adjust pH to 7.2 | Adjust pH to 7.2 | Adjust pH to 7.2 |
| Hydrochloric Acid 1N | Adjust pH to 7.2 | Adjust pH to 7.2 | Adjust pH to 7.2 | Adjust pH to 7.2 |
| Purified water | q.s. ad. | q.s. ad. | q.s. ad | q.s. ad. |

[(1)]Purite ® is a registered trademark of Allergan, Inc. for stabilized chlorine dioxide. This material is added to the mixture after heat sterilization.
[(3)]A mixture of 10% by weight high molecular weight carboxylmethyl cellulose having a weight average molecular weight of about 700,000, and 90% by weight medium molecular weight carboxymethyl cellulose having a weight average molecular weight of about 250,000.

EXAMPLE 17

Each of the compositions produced in Examples 10 through 16, in the form of eye drops, is administered once a day or more often to the eyes of a patient suffering from dry eye syndrome. Administration may be either in response to or in anticipation of exposure to adverse environmental conditions for example dry or windy environments, low humidity, extensive computer use, and the like. Such administration is substantially similar to that used with conventional artificial tear compositions.

All of the patients, after one week of such administration, are found to have received substantial relief, for example, in terms of reduced pain and/or reduced irritation and/or enhanced vision and/or enhanced eye appearance, from the effects or symptoms of dry eye syndrome. In addition, those patients who are administered compositions including carboxymethyl cellulose (CMC) are found to have benefited from the anionic character of the CMC and the relatively increased viscosities of such compositions. Such benefits include, without limitation, reduced irritation for longer periods of time after administration, and/or enhanced eye lubrication and/or enhanced protection against adverse effects of cationic species on the ocular surfaces of the patient's eyes.

EXAMPLE 18

Each of the compositions produced in Examples 10 through 16 including carboxymethyl cellulose (CMC), in the form of eye drops, is administered to an eye of a different human patient about to undergo a LASIK surgical procedure.

After the surgical procedure, each of the patients has reduced pain and/or reduced discomfort and/or reduced eye irritation and/or more rapid recovery from the surgical procedure relative to undergoing an identical surgical procedure including being administered the same composition without the carboxymethyl cellulose.

EXAMPLE 19

Each of the compositions produced in Examples 10 through 16 including carboxymethyl cellulose, in the form of eye drops, is administered to the eye of a different human patient undergoing a LASIK surgical procedure.

After the surgical procedure, each of the patients has reduced pain and/or reduced discomfort and/or reduced eye irritation and/or more rapid recovery from the surgical procedure relative to undergoing an identical surgical procedure including being administered the same composition without the carboxymethyl cellulose.

EXAMPLE 20

Each of the compositions produced in Examples 10 through 16 including carboxymethyl cellulose, in the form of eye drops, is administered to the eye of a different human patient substantially immediately after undergoing a LASIK surgical procedure.

Each patient has reduced pain and/or reduced discomfort and/or reduced eye irritation and/or more rapid recovery from the surgical procedure relative to undergoing an identical surgical procedure including being administered the same composition without the carboxymethyl cellulose.

While this invention has been described with respect to various specific examples and embodiments, it is to be understood that the invention is not limited thereto and that it can be variously practiced within the scope of the following claims.

What is claimed is:

1. A topical ophthalmic composition for the treatment of dry eye comprising:
   water;
   a tonicity component selected from erythritol, carnitine, isomers thereof, and suitable salts thereof;
   carboxymethyl cellulose or its suitable salt, or a combination of carboxymethylcellulose or its suitable salt and hyaluronic acid; and
   glycerol;
   wherein the composition is effective for the treatment of dry eye.

2. The composition of claim 1, further comprising a buffer selected from the group consisting of sodium citrate and sodium borate, and a salt selected from the group consisting of potassium chloride, calcium chloride, and magnesium chloride.

3. The composition of claim 1, wherein the carboxymethly cellulose is present in an amount of about 0.5 to about 1.0% w/v.

4. The composition of claim 1, wherein erythritol, its isomer, and/or its suitable salt is present in an amount of about 0.05% to about 1% w/v.

5. The composition of claim 1, wherein carnitine, its isomer, and/or its suitable salt is present in an amount of about 0.05% to about 1% w/v.

6. The composition of claim 1, wherein the carboxymethylcellulose or its suitable salt or combination of carboxymethylcellulose or its suitable salt and hyaluronic acid is present in an amount between about 0.4% w/v to about 1.3% w/v.

7. The composition of claim 1, wherein the hyaluronic acid is present in an amount of about 0.1% w/v.

\* \* \* \* \*

UNITED STATES PATENT AND TRADEMARK OFFICE
CERTIFICATE OF CORRECTION

PATENT NO. : 10,213,405 B2
APPLICATION NO. : 15/585888
DATED : February 26, 2019
INVENTOR(S) : Joseph G. Vehige et al.

It is certified that error appears in the above-identified patent and that said Letters Patent is hereby corrected as shown below:

In the Drawings

On sheet 3 of 8, in Figure 3, Line 1 (x-axis), delete "Mln" and insert -- Min --, therefor.

On sheet 3 of 8, in Figure 3, Line 1 (x-axis), delete "CN400" and insert -- CN 400 --, therefor.

On sheet 4 of 8, in Figure 4, Line 1 (x-axis), delete "Mln" and insert -- Min --, therefor.

On sheet 4 of 8, in Figure 4, Line 1 (x-axis), delete "CN400" and insert -- CN 400 --, therefor.

On sheet 5 of 8, in Figure 5, Line 1 (x-axis), delete "Mln" and insert -- Min --, therefor.

On sheet 5 of 8, in Figure 5, Line 1 (x-axis), delete "CN400" and insert -- CN 400 --, therefor.

In the Specification

In Column 11, Line 6, delete "IhIrsetstf" and insert -- Ihirsetstf --, therefor.

In Column 11, Line 6, delete "eetperelee" and insert -- eetpcrelee --, therefor.

In Column 12, Line 26, delete "polyacrylam ides" and insert -- polyacrylamides --, therefor.

In Column 12, Line 28, delete "glycoam inoglycans" and insert -- glycosaminoglycans --, therefor.

In Column 12, Line 46, delete "2-methacryloyloxethylsulfonates" and insert -- 2-methacryloyloxyethylsulfonates --, therefor.

In Column 22, Line 52, delete "Purite7" and insert -- Purite® --, therefor.

In Column 23, Line 18, delete "carboxylmethyl" and insert -- carboxymethyl --, therefor.

Signed and Sealed this
Twenty-first Day of May, 2019

Andrei Iancu
*Director of the United States Patent and Trademark Office*

In the Claims

In Column 26, Lines 21-22, in Claim 3, delete "carboxymethly" and insert -- carboxymethyl --, therefor.